US012594056B2

(12) United States Patent (10) Patent No.: US 12,594,056 B2
Tsubota et al. (45) Date of Patent: Apr. 7, 2026

(54) ULTRASOUND SYSTEM AND METHOD FOR CONTROLLING ULTRASOUND SYSTEM

(71) Applicant: FUJIFILM Corporation, Tokyo (JP)

(72) Inventors: Keiji Tsubota, Kanagawa (JP); Tomoki Inoue, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 781 days.

(21) Appl. No.: 17/074,030

(22) Filed: Oct. 19, 2020

(65) Prior Publication Data

US 2021/0030399 A1 Feb. 4, 2021

Related U.S. Application Data

(63) Continuation of application No. PCT/JP2019/019232, filed on May 15, 2019.

(30) Foreign Application Priority Data

May 25, 2018 (JP) ................................. 2018-100919

(51) Int. Cl.
    *A61B 8/00* (2006.01)
    *G06F 3/04845* (2022.01)
    *G06F 3/0488* (2022.01)

(52) U.S. Cl.
    CPC ............ *A61B 8/465* (2013.01); *A61B 8/4472* (2013.01); *A61B 8/4483* (2013.01); *A61B 8/463* (2013.01);
    (Continued)

(58) Field of Classification Search
    CPC ......... A61B 8/465; A61B 8/467; A61B 8/463; A61B 8/4483; A61B 8/4472; A61B 8/54; G06F 3/04845; G06F 3/0488
    See application file for complete search history.

(56) References Cited

U.S. PATENT DOCUMENTS

2005/0075566 A1* 4/2005 Satoh ..................... A61B 8/469
                                                          600/443
2012/0296212 A1 11/2012 Hamada et al.
                        (Continued)

FOREIGN PATENT DOCUMENTS

JP       2010-44520 A    2/2010
JP       2012-105968 A   6/2012
                 (Continued)

OTHER PUBLICATIONS (T, Anthony. "Finger-Friendly Design: Ideal Mobile Touchscreen Target Sizes." Smashing Magazine, Feb. 21, 2012, https://www. smashingmagazine.com/2012/02/finger-friendly-design-ideal-mobile-touchscreen-target sizes/#:~:text=An%20MIT%20Touch%20Lab% 20study,20%20mm)%20for%20most%20adults.).*

(Continued)

*Primary Examiner* — Christopher L Cook
(74) *Attorney, Agent, or Firm* — Studebaker Brackett PLLC

(57) ABSTRACT

An ultrasound system 1 includes: a display unit 34 that displays an acquired ultrasound image as a first image in an image display region; an operation unit 40 that includes a touch sensor disposed so as to be superimposed on the image display region and is used by a user to perform a touch input operation; a second image generation unit 37 that generates a second image indicating a partial image which corresponds to a predetermined region including a touch position of the user in the first image; and a second image display position determination unit 38 that determines a position different from the touch position in the image display region as a display position of the second image on the basis of the touch position. In a case in which the image display region is touched by the user, the second image is displayed at the
(Continued)

determined display position so as to be superimposed on the first image.

11 Claims, 11 Drawing Sheets

(52) U.S. Cl.
CPC ............ *A61B 8/467* (2013.01); *A61B 8/5207* (2013.01); *A61B 8/54* (2013.01); *G06F 3/04845* (2013.01); *G06F 3/0488* (2013.01)

(56) References Cited

U.S. PATENT DOCUMENTS

| | | | |
|---|---|---|---|
| 2014/0114190 A1 | 4/2014 | Chiang et al. | |
| 2014/0121524 A1* | 5/2014 | Chiang ................ | A61B 8/0891 600/459 |
| 2014/0184519 A1* | 7/2014 | Benchenaa .......... | G06F 1/1626 345/173 |
| 2015/0141823 A1* | 5/2015 | Lee ........................ | A61B 8/467 600/440 |
| 2016/0231862 A1* | 8/2016 | Tretter ...................... | G06T 7/12 |
| 2017/0090675 A1* | 3/2017 | Lee ........................ | A61B 8/469 |
| 2017/0364206 A1* | 12/2017 | Eberbach .............. | G06F 3/0488 |
| 2019/0278431 A1* | 9/2019 | Dunning .......... | G06Q 10/06315 |

FOREIGN PATENT DOCUMENTS

| | | |
|---|---|---|
| JP | 2015-107200 A | 6/2015 |
| JP | 2016-516465 A | 6/2016 |
| JP | 2017-213427 A | 12/2017 |

OTHER PUBLICATIONS

An Office Action; "Notice of Reasons for Refusal", mailed by the Japanese Patent Office on Dec. 14, 2021, which corresponds to Japanese Patent Application No. 2020-521173 and is related to U.S. Appl. No. 17/074,030; with English language translation.
International Search Report issued in PCT/JP2019/019232; mailed Aug. 13, 2019.
International Preliminary Report On Patentability and Written Opinion issued in PCT/JP2019/019232; issued Dec. 1, 2020.
An Office Action; "Notice of Reasons for Refusal", mailed by the Japanese Patent Office on Jun. 14, 2022, which corresponds to Japanese Patent Application No. 2020-521173 and is related to U.S. Appl. No. 17/074,030; with English language translation.

\* cited by examiner

ULTRASOUND SYSTEM AND METHOD FOR CONTROLLING ULTRASOUND SYSTEM

CROSS-REFERENCE TO RELATED APPLICATIONS

This application is a Continuation of PCT International Application No. PCT/JP2019/019232 filed on May 15, 2019, which claims priority under 35 U.S.C. § 119(a) to Japanese Patent Application No. 2018-100919 filed on May 25, 2018. The above application is hereby expressly incorporated by reference, in its entirety, into the present application.

BACKGROUND OF THE INVENTION

1. Field of the Invention

The present invention relates to an ultrasound system and a method for controlling the ultrasound system, and more particularly, to an ultrasound system comprising a touch sensor and a method for controlling the ultrasound system.

In the related art, an ultrasound diagnostic apparatus using an ultrasound image has been put to practical use in the medical field. In general, this type of ultrasound diagnostic apparatus includes an ultrasound probe having a transducer array provided therein and an apparatus main body connected to the ultrasound probe. Ultrasonic waves are transmitted from the ultrasound probe to a subject. The ultrasound probe receives ultrasound echoes from the subject. The apparatus main body electrically processes a reception signal to generate an ultrasound image.

In recent years, for example, as disclosed in JP2016-516465A, an ultrasound system has come into widespread use in which an operation unit used by a user to perform an input operation comprises a touch sensor. In general, the touch sensor is disposed so as to be superimposed on a display screen of a display unit and is used for an input operation by a so-called touch operation of bringing a user's finger, a stylus pen, and the like into contact with or close to the display screen. In the ultrasound system disclosed in JP2016-516465A, a touch region image indicating a predetermined region including a touch position of the user on the display screen is displayed at a predetermined position on the display screen.

SUMMARY OF THE INVENTION

However, in the ultrasound system disclosed in JP2016-516465A, a region for displaying the touch region image is provided in the display screen in addition to a region for displaying an ultrasound image. The region for displaying the touch region image is always displayed. Therefore, there is a problem that it is difficult to effectively display the ultrasound image. For example, the region for displaying the ultrasound image is narrowed.

The invention has been made in order to solve the problems of the related art and an object of the invention is to provide an ultrasound system that can effectively display an ultrasound image while enabling a user to clearly understand a touch position and a method for controlling the ultrasound system.

In order to achieve the above object, according to the invention, there is provided an ultrasound system comprising: a display unit that displays an acquired ultrasound image as a first image in an image display region; an operation unit that includes a touch sensor disposed so as to be superimposed on the image display region and is used by a user to perform a touch input operation; a second image generation unit that generates a second image indicating a partial image which corresponds to a predetermined region including a touch position of the user in the first image displayed in the image display region; and a second image display position determination unit that determines a display position which is a position different from the touch position in the image display region and is for displaying the second image on the basis of the touch position. In a case in which the image display region in which the first image is displayed is touched by the user, the second image generated by the second image generation unit is displayed at the display position determined by the second image display position determination unit so as to be superimposed on the first image displayed in the image display region.

The second image generation unit may include: an image size setting unit that sets a size of the second image displayed in the image display region; and an image cutout unit that cuts out, from the first image, an image which corresponds to the predetermined region and has the size set by the image size setting unit.

In this case, the image size setting unit may set the size of the second image to a predetermined size.

Further, the image display region may be a rectangular region that extends in a first direction and a second direction orthogonal to each other, and the image size setting unit may set a dimension of the second image in the first direction to be equal to or less than half of a dimension of the image display region in the first direction and may set a dimension of the second image in the second direction to be equal to or less than half of a dimension of the image display region in the second direction.

Alternatively, the image size setting unit may set the size of the second image to a size that is equal to or greater than an average value of a width of a finger based on statistical data.

In addition, the second image generation unit may include a finger width detection unit that detects a width of a finger of the user touching the image display region in a case in which the finger of the user touches the image display region, and the image size setting unit may set the size of the second image on the basis of the width of the finger of the user detected by the finger width detection unit.

Further, the ultrasound system may further comprise a second image adjustment unit that changes at least one of the size of the second image generated by the second image generation unit or the display position of the second image determined by the second image display position determination unit according to an operation of the user and displays the second image in the image display region.

In addition, the second image generation unit may generate an image that has the same size as the predetermined region in the first image.

Alternatively, the second image generation unit may generate an image obtained by enlarging the predetermined region in the first image.

Further, the ultrasound system may further comprise a measurement unit that displays a measurement cursor so as to be superimposed on the first image and performs measurement for the ultrasound image on the basis of the measurement cursor. In a case in which the measurement cursor is touched by the user, the second image generation unit may generate the second image including the measurement cursor.

In this case, preferably, in a case in which there are a plurality of the touch positions in the image display region, the second image generation unit generates the second image corresponding to the predetermined region including a touch position that is closest to the measurement cursor.

Further, preferably, in a case in which there are a plurality of the touch positions in the image display region, the second image display position determination unit determines a position that is farthest from the plurality of touch positions in the image display region as the display position of the second image.

Furthermore, preferably, the image display region is a rectangular region having an upper edge portion and a lower edge portion, and the second image display position determination unit determines, as the display position of the second image, a position except a region on a perpendicular line drawn perpendicularly to the lower edge portion of the image display region from the touch position in the image display region.

Further, the ultrasound system may further comprise an ultrasound probe and a diagnostic apparatus main body that are wirelessly connected to each other. The ultrasound probe may include: a transducer array; a transmitting and receiving unit that transmits ultrasonic waves from the transducer array and generates a sound ray signal on the basis of a reception signal acquired by the transducer array; an image information data generation unit that generates image information data on the basis of the sound ray signal generated by the transmitting and receiving unit; and a wireless communication unit that wirelessly transmits the image information data generated by the image information data generation unit to the diagnostic apparatus main body. The diagnostic apparatus main body may include: the display unit that displays the ultrasound image on the basis of the image information data wirelessly transmitted from the ultrasound probe; the operation unit; the second image generation unit; and the second image display position determination unit.

In this case, preferably, the image information data is a signal obtained by performing attenuation correction according to a depth of a reflection position of the ultrasonic waves and an envelope detection process on the sound ray signal generated by the transmitting and receiving unit.

Alternatively, the image information data may be an ultrasound image signal obtained by performing attenuation correction according to a depth of a reflection position of the ultrasonic waves and an envelope detection process on the sound ray signal generated by the transmitting and receiving unit and converting the sound ray signal according to a predetermined image display method.

According to the invention, there is provided a method for controlling an ultrasound system. The method comprises: displaying an acquired ultrasound image as a first image in an image display region; generating a second image indicating a partial image which corresponds to a predetermined region including a touch position of a user in the first image displayed in the image display region; determining a display position which is a position different from the touch position in the image display region and is for displaying the second image on the basis of the touch position; and displaying the second image at the display position so as to be superimposed on the first image displayed in the image display region in a case in which the image display region in which the first image is displayed is touched by the user.

According to the invention, the ultrasound system includes the operation unit that includes the touch sensor disposed so as to be superimposed on the image display region and is used by the user to perform a touch input operation; the second image generation unit that generates the second image indicating the partial image which corresponds to the predetermined region including the touch position of the user in the first image displayed in the image display region; and the second image display position determination unit that determines the display position which is a position different from the touch position in the image display region and is for displaying the second image on the basis of the touch position. In a case in which the image display region in which the first image is displayed is touched by the user, the second image generated by the second image generation unit is displayed at the display position determined by the second image display position determination unit so as to be superimposed on the first image displayed in the image display region. Therefore, it is possible to more effectively display the ultrasound image while enabling the user to clearly understand the touch position.

DESCRIPTION OF THE PREFERRED EMBODIMENTS

Embodiments of the invention will be described below with reference to the accompanying drawings.

Embodiment 1

Figure 1:
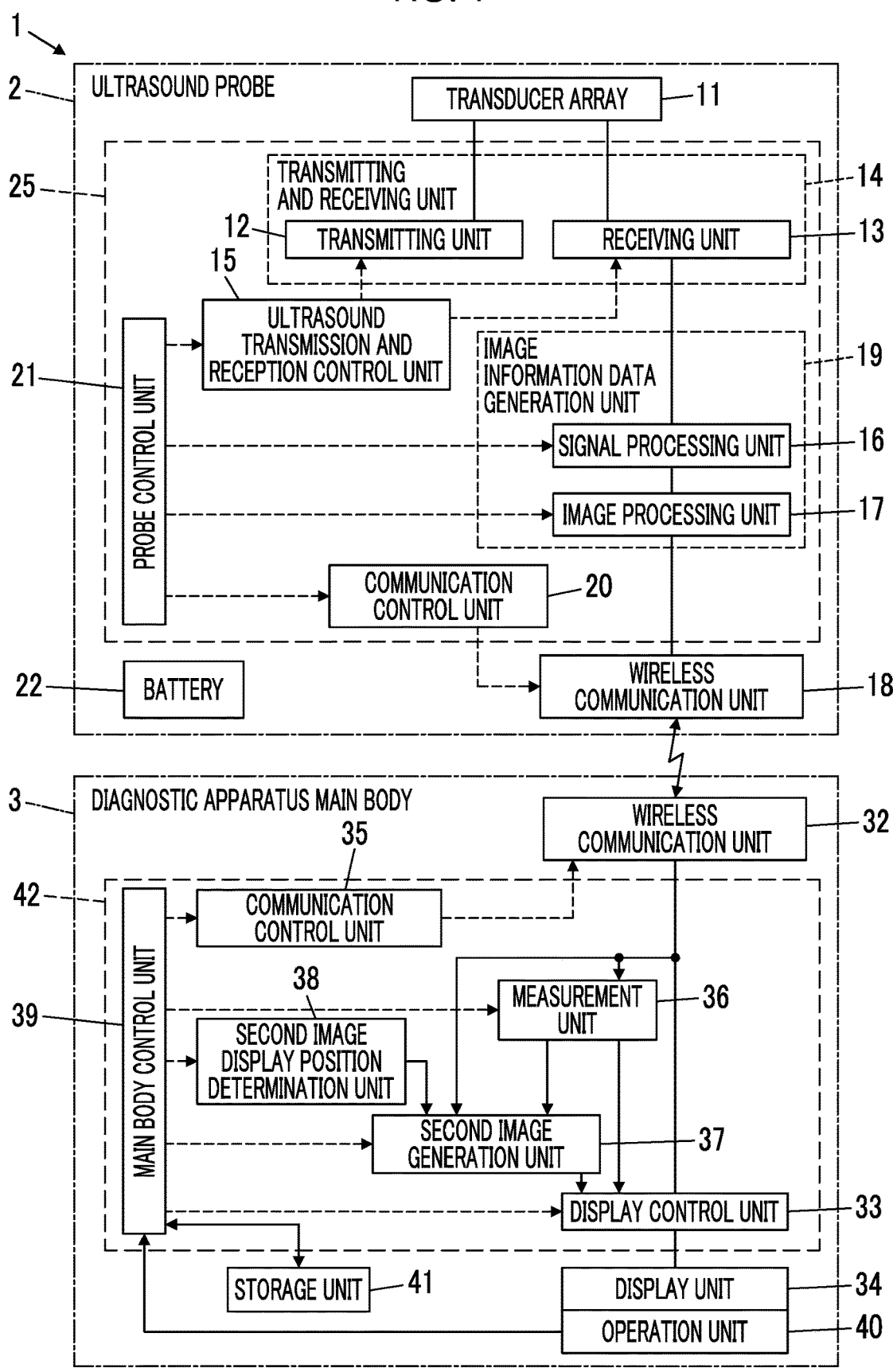
FIG. 1 is a block diagram illustrating a configuration of an ultrasound system according to Embodiment 1 of the invention.

FIG. 1 illustrates the configuration of an ultrasound system 1 according to Embodiment 1 of the invention. As illustrated in FIG. 1, the ultrasound system 1 comprises an ultrasound probe 2 and a diagnostic apparatus main body 3. The ultrasound probe 2 and the diagnostic apparatus main body 3 are connected to each other by wireless communication.

The ultrasound probe 2 of the ultrasound system 1 comprises a transducer array 11. The transducer array 11 is connected to a transmitting unit 12 and a receiving unit 13. The transmitting unit 12 and the receiving unit 13 form a transmitting and receiving unit 14. An ultrasound transmission and reception control unit 15 is connected to the transmitting unit 12 and the receiving unit 13. A signal processing unit 16, an image processing unit 17, and a wireless communication unit 18 are sequentially connected to the receiving unit 13. The signal processing unit 16 and the image processing unit 17 form an image information data generation unit 19.

Further, a communication control unit 20 is connected to the wireless communication unit 18. Furthermore, a probe control unit 21 is connected to the ultrasound transmission and reception control unit 15, the signal processing unit 16, the image processing unit 17, and the communication control unit 20. In addition, the ultrasound probe 2 has a battery 22 provided therein. Further, a probe-side processor 25 is configured by the transmitting and receiving unit 14, the ultrasound transmission and reception control unit 15, the image information data generation unit 19, the communication control unit 20, and the probe control unit 21.

The diagnostic apparatus main body 3 of the ultrasound system 1 comprises a wireless communication unit 32. A display control unit 33 and a display unit 34 are sequentially connected to the wireless communication unit 32. Further, a communication control unit 35, a measurement unit 36, and a second image generation unit 37 are connected to the wireless communication unit 32. The measurement unit 36 and the second image generation unit 37 are connected to the display control unit 33. Furthermore, the measurement unit 36 and a second image display position determination unit 38 are connected to the second image generation unit 37. In addition, an operation unit 40 is disposed so as to be superimposed on the display unit 34.

Further, a main body control unit 39 is connected to the display control unit 33, the communication control unit 35, the measurement unit 36, the second image generation unit 37, the second image display position determination unit 38, and the operation unit 40. A storage unit 41 is connected to the main body control unit 39 such that information can be bidirectionally transmitted and received.

Furthermore, a main-body-side processor 42 is configured by the display control unit 33, the communication control unit 35, the measurement unit 36, the second image generation unit 37, the second image display position determination unit 38, and the main body control unit 39.

The transducer array 11 of the ultrasound probe 2 has a plurality of ultrasound transducers which are arranged one-dimensionally or two-dimensionally. Each of the transducers transmits ultrasonic waves according to a driving voltage signal supplied from the transmitting unit 12, receives waves reflected from a subject, and outputs a reception signal. Each transducer is configured using an element in which electrodes are formed at both ends of a piezoelectric body consisting of, for example, a piezoelectric ceramic typified by lead zirconate titanate (PZT), a polymeric piezoelectric element typified by polyvinylidene difluoride (PVDF), and a piezoelectric single crystal typified by lead magnesium niobate-lead titanate (PMN-PT).

The transmitting unit 12 of the transmitting and receiving unit 14 includes, for example, a plurality of pulse generators, adjusts the amount of delay of each driving signal on the basis of a transmission delay pattern selected according to a control signal from the ultrasound transmission and reception control unit 15 such that the ultrasonic waves transmitted from the plurality of transducers of the transducer array 11 form an ultrasound beam, and supplies the driving signals to the plurality of transducers. As such, in a case in which a pulsed or continuous-wave voltage is applied to the electrodes of the transducers of the transducer array 11, the piezoelectric body is expanded and contracted and pulsed or continuous ultrasonic waves are generated from each transducer. An ultrasound beam is formed from a combined wave of the ultrasonic waves.

The transmitted ultrasound beam is reflected by a target, such as a part of the subject, and is propagated toward the transducer array 11. The ultrasonic waves propagated toward the transducer array 11 in this way are received by each of the ultrasound transducers forming the transducer array 11. In this case, each of the ultrasound transducers forming the transducer array 11 receives propagated ultrasound echoes, is expanded and contracted to generate an electric signal, and outputs a reception signal which is the electric signal to the receiving unit 13.

Figure 2:
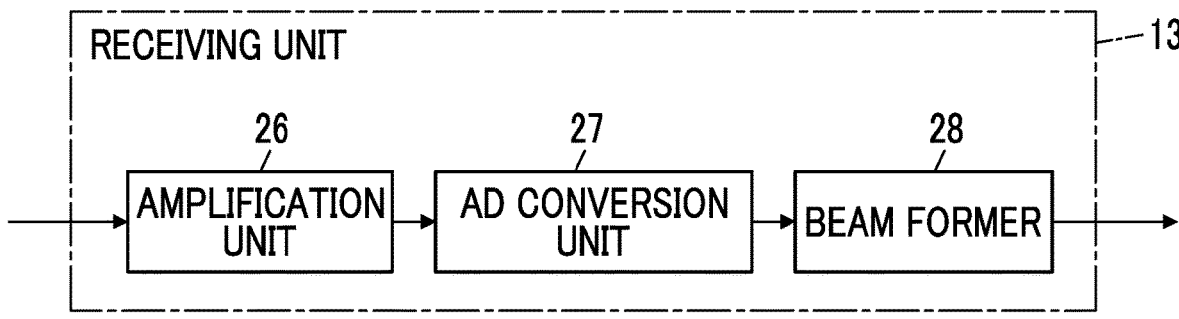
FIG. 2 is a block diagram illustrating an internal configuration of a receiving unit in Embodiment 1 of the invention.

The receiving unit 13 of the transmitting and receiving unit 14 processes the reception signal output from the transducer array 11 according to a control signal from the ultrasound transmission and reception control unit 15. As illustrated in FIG. 2, the receiving unit 13 has a configuration in which an amplification unit 26, an analog digital (AD) conversion unit 27, and a beam former 28 are connected in series to each other. The amplification unit 26 amplifies the reception signal input from each of the transducers forming the transducer array 11 and transmits the amplified reception signal to the AD conversion unit 27. The AD conversion unit 27 converts the reception signal transmitted from the amplification unit 26 into digital element data and transmits the element data to the beam former 28. The beam former 28 performs a reception focusing process which gives a delay to each element data item following the set sound velocity on the basis of a reception delay pattern selected according to a control signal from the ultrasound transmission and reception control unit 15 and performs addition (phasing addition). The sound ray signal in which the focus of the ultrasound echo is narrowed is generated by the reception focusing process.

The ultrasound transmission and reception control unit 15 of the probe-side processor 25 controls the transmitting unit 12 and the receiving unit 13 of the transmitting and receiving unit 14 to perform the transmission of ultrasound beams and the reception of ultrasound echoes on the basis of an inspection mode and a scanning method instructed by the probe control unit 21. Here, it is assumed that the inspection mode indicates any one of the inspection modes that can be used in the ultrasound diagnostic apparatus, such as a brightness (B) mode, a motion (M) mode, a color Doppler (CD) mode, a power Doppler (PD) mode, a pulse Doppler (PW) mode, and a continuous wave Doppler (CW), and the scanning method indicates any one of scanning methods, such as an electronic sector scanning method, an electronic linear scanning method, and an electronic convex scanning method.

The signal processing unit 16 of the image information data generation unit 19 corrects the attenuation of the sound ray signal generated by the beam former 28 of the receiving unit 13 caused by a propagation distance according to the depth of the position where the ultrasonic waves are reflected and performs an envelope detection process on the sound ray signal to generate a signal which is tomographic image information related to the tissues in the subject.

The image processing unit 17 of the image information data generation unit 19 raster-converts the signal generated by the signal processing unit 16 into an image signal following a general television signal scanning method, performs various types of necessary image processing, such as brightness correction, gradation correction, sharpness correction, and color correction, on the generated image signal to generate an ultrasound image signal, and transmits the ultrasound image signal as image information data to the wireless communication unit 18 of the ultrasound probe 2.

The wireless communication unit 18 of the ultrasound probe 2 is configured by, for example, a circuit including an antenna for transmitting and receiving radio waves and performs wireless communication with the wireless communication unit 32 of the diagnostic apparatus main body 3. In this case, the wireless communication unit 18 of the ultrasound probe 2 modulates a carrier on the basis of the ultrasound image signal generated by the image processing unit 17 of the image information data generation unit 19 to generate a transmission signal indicating the ultrasound image signal and wirelessly transmits the generated transmission signal to the wireless communication unit 32 of the diagnostic apparatus main body 3. For example, amplitude shift keying (ASK), phase shift keying (PSK), quadrature phase shift keying (QPSK), and 16 quadrature amplitude modulation (16QAM) are used as the carrier modulation method.

The probe control unit 21 of the probe-side processor 25 controls each unit of the ultrasound probe 2 on the basis of, for example, a program stored in advance.

The battery 22 of the ultrasound probe 2 is provided in the ultrasound probe 2 and supplies power to each circuit of the ultrasound probe 2.

The communication control unit 20 of the probe-side processor 25 controls the wireless communication unit 18 of the ultrasound probe 2 such that the ultrasound image signal is transmitted with transmission radio field intensity set by the probe control unit 21.

The wireless communication unit 32 of the diagnostic apparatus main body 3 is configured by, for example, a circuit including an antenna for transmitting and receiving radio waves and performs wireless communication with the wireless communication unit 18 of the ultrasound probe 2. In this case, the wireless communication unit 32 of the diagnostic apparatus main body 3 receives, for example, the transmission signal indicating the ultrasound image signal wirelessly transmitted from the wireless communication unit 18 of the ultrasound probe 2 through the antenna, demodulates the received transmission signal, and outputs the ultrasound image signal.

Further, the communication control unit 35 of the main-body-side processor 42 controls the wireless communication unit 32 of the diagnostic apparatus main body 3 such that the transmission signal is received from the wireless communication unit 18 of the ultrasound probe 2.

The display control unit 33 of the main-body-side processor 42 performs predetermined processing on the ultrasound image signal output from the wireless communication unit 32 of the diagnostic apparatus main body 3 and displays an ultrasound image as a first image on the display unit 34 under the control of the main body control unit 39. In addition to the ultrasound image, the display control unit 33 displays, for example, a measurement cursor generated by the measurement unit 36 and a second image generated by the second image generation unit 37 on the display unit 34, which will be described below.

Figure 3:
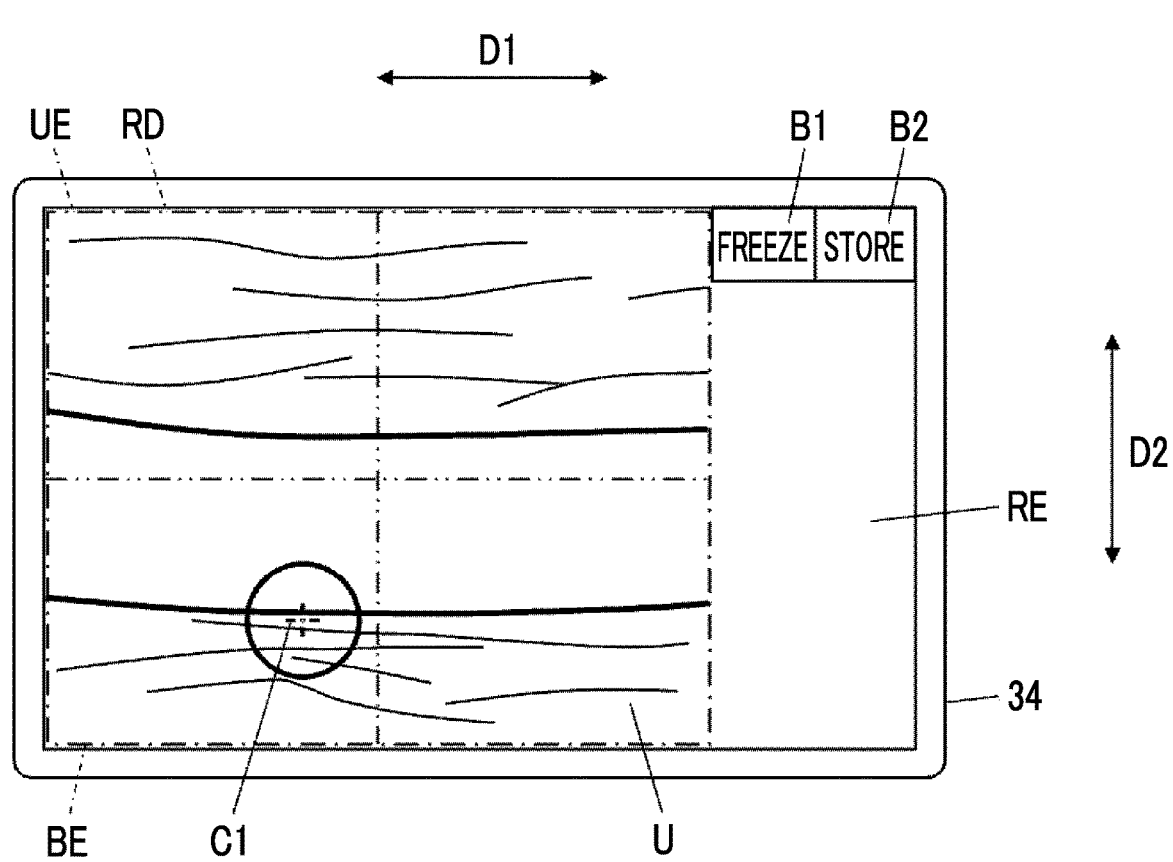
FIG. 3 is a diagram schematically illustrating an image display region and an outer region set in a display unit in Embodiment 1 of the invention.

The display unit 34 of the diagnostic apparatus main body 3 displays, for example, the ultrasound image under the control of the display control unit 33. In this case, as illustrated in FIG. 3, an image display region RD for displaying the ultrasound image is set in the display unit 34, and the ultrasound image is displayed in the image display region RD. Here, the image display region RD is a rectangular region that extends in a first direction D1 and a second direction D2 orthogonal to each other and has an upper edge portion UE and a lower edge portion BE. Further, in the display unit 34, an outer region RE is set outside the image display region RD, and buttons used for the input operation of the user can be displayed in the outer region RE. In the example illustrated in FIG. 3, a freeze button B1 for the freeze display of the ultrasound image and a storage button B2 for storing the ultrasound image displayed in the image display region RD are displayed in the outer region RE.

The display unit 34 includes a display device such as a liquid crystal display (LCD) or an organic electroluminescence (EL) display.

The operation unit 40 of the diagnostic apparatus main body 3 is used by the user to perform an input operation and includes a touch sensor that is disposed so as to be superimposed on the display unit 34. The touch sensor is disposed so as to be superimposed on a display screen of the display unit 34 and is used for an input operation by a so-called touch operation of bringing a user's finger, a stylus pen, and the like into contact with or close to the display screen. Input information input by the user through the touch sensor of the operation unit 40 is transmitted to the main body control unit 39.

The measurement unit 36 of the main-body-side processor 42 measures, for example, a distance and an area on the ultrasound image. In this case, for example, as illustrated in FIG. 3, the measurement unit 36 generates a measurement cursor C1 for measuring the distance on an ultrasound image U and displays the measurement cursor C1 so as to be superimposed on the ultrasound image U displayed in the image display region RD of the display unit 34. The user touches and drags the displayed measurement cursor C1 used for measurement for the ultrasound image U to move the measurement cursor C1. The measurement unit 36 can measure the distance on the ultrasound image U on the basis of, for example, the position of the moved measurement cursor C1.

Figure 4:
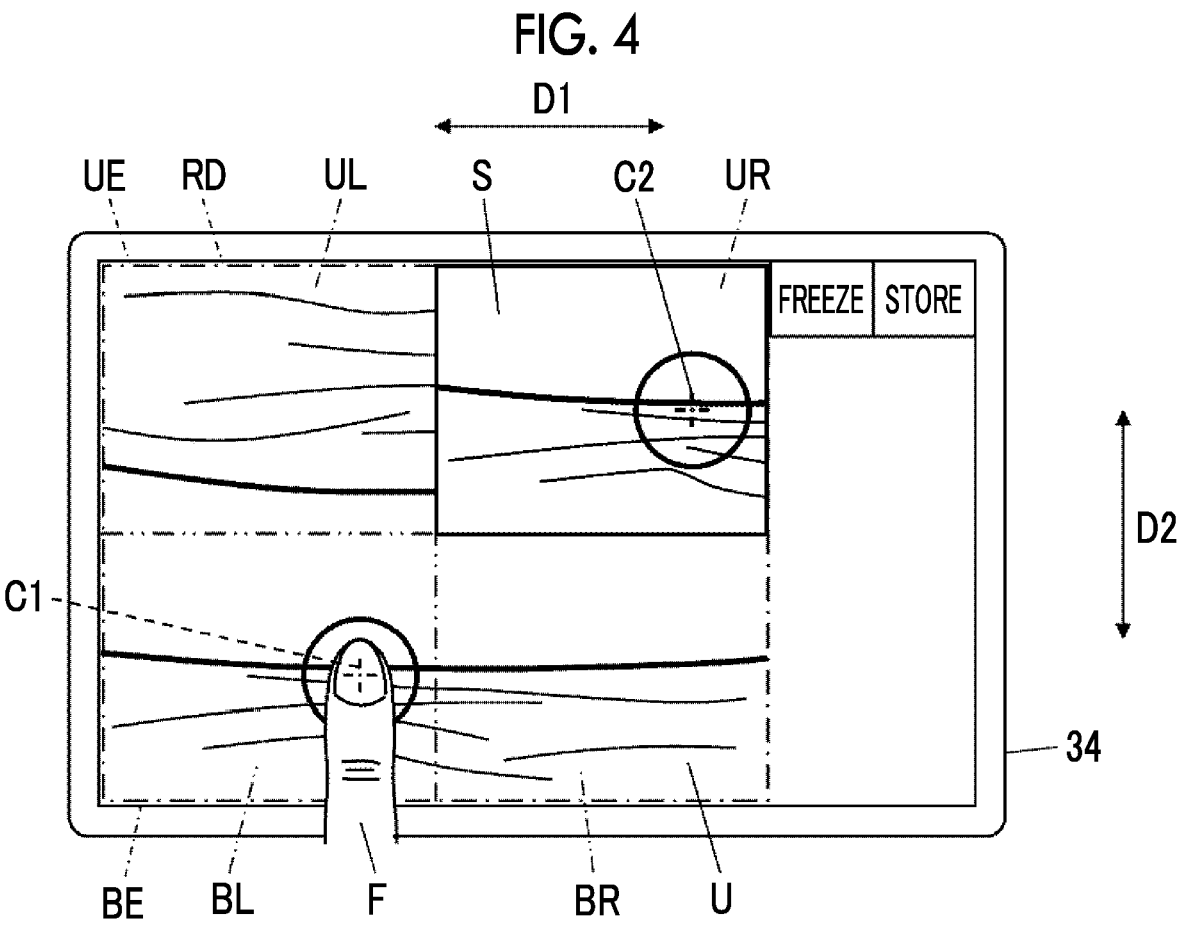
FIG. 4 is a diagram schematically illustrating a second image in Embodiment 1 of the invention.
Figure 5:
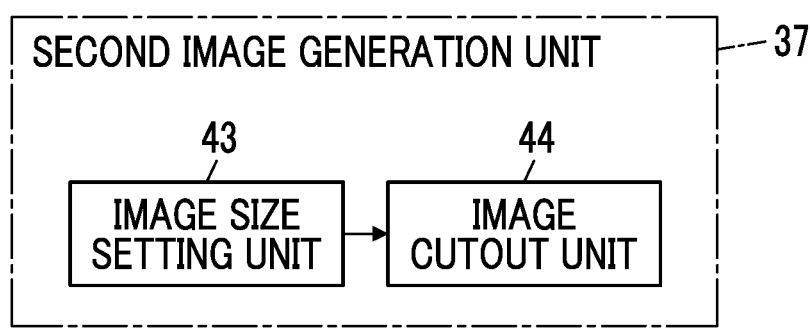
FIG. 5 is a block diagram illustrating an internal configuration of a second image generation unit in Embodiment 1 of the invention.

The second image generation unit 37 of the main-body-side processor 42 generates the second image on the basis of the touch position of the user in the image display region RD of the display unit 34 and the ultrasound image U displayed in the image display region RD and displays the generated second image in the image display region RD. Here, as illustrated in FIG. 4, the second image is a partial image that corresponds to a predetermined region including the touch position of the user in the ultrasound image U. As illustrated in FIG. 5, the second image generation unit 37 includes an image size setting unit 43 and an image cutout unit 44, and the image size setting unit 43 and the image cutout unit 44 are connected to each other.

The image size setting unit 43 of the second image generation unit 37 sets the size of the second image under the control of the main body control unit 39. For example, the image size setting unit 43 sets the size of the second image to a predetermined size.

The image cutout unit 44 of the second image generation unit 37 cuts out an image of a region that includes the touch position of the user and has the size set by the image size setting unit 43 from the ultrasound image U displayed in the image display region RD and generates the second image.

Here, in the example illustrated in FIG. 4, the image display region RD is divided into four regions of an upper left region UL, an upper right region UR, a lower left region BL, and a lower right region BR. A second image S is an image having the same size as the ultrasound image U of the lower left region BL touched by a finger F of the user among the four regions, that is, a cut-out image of the ultrasound image U of the lower left region BL.

The second image display position determination unit 38 of the main-body-side processor 42 determines a position which is different from the touch position of the user in the image display region RD as a display position for displaying the second image S on the basis of the touch position of the user in the image display region RD of the display unit 34. In the example illustrated in FIG. 4, the second image display position determination unit 38 determines the upper right region UR which is different from the lower left region BL of the image display region RD touched by the finger F of the user as the display position of the second image S. As such, since a position different from the touch position of the user is determined as the display position of the second image S, the second image S does not hinder the touch operation of the user and the user can clearly understand the touch position hidden by the finger F.

The main body control unit 39 of the main-body-side processor 42 controls each unit of the diagnostic apparatus main body 3 on the basis of the program stored in advance in, for example, the storage unit 41 and the input operation of the user through the operation unit 40.

The storage unit 41 of the diagnostic apparatus main body 3 stores, for example, an operation program for the diagnostic apparatus main body 3. The following can be used as the storage unit 41: a semiconductor memory, such as flash memory, read only memory (ROM), or a random access memory (RAM); a recording medium, such as a hard disc drive (HDD), a solid state drive (SSD), a flexible disc (FD), a magneto-optical disc (MO disc), a magnetic tape (MT), a compact disc (CD), a digital versatile disc (DVD), a secure digital card (SD card), or a universal serial bus memory (USB memory); or a sever.

Here, the probe-side processor 25 including the transmitting and receiving unit 14, the ultrasound transmission and reception control unit 15, the image information data generation unit 19, the communication control unit 20, and the probe control unit 21 in the ultrasound probe 2 and the main-body-side processor 42 including the display control unit 33, the communication control unit 35, the measurement unit 36, the second image generation unit 37, the second image display position determination unit 38, and the main body control unit 39 in the diagnostic apparatus main body 3 are implemented by a central processing unit (CPU) and a control program for causing the CPU to perform various processes. However, the processors may be implemented by a field programmable gate array (FPGA), a digital signal processor (DSP), an application specific integrated circuit (ASIC), a graphics processing unit (GPU), other integrated circuits (ICs), or combinations thereof.

Some or all of the transmitting and receiving unit 14, the ultrasound transmission and reception control unit 15, the communication control unit 20, and the probe control unit 21 of the probe-side processor 25 may be integrated into, for example, one CPU. Similarly, some or all of the display control unit 33, the communication control unit 35, the measurement unit 36, the second image generation unit 37, the second image display position determination unit 38, and the main body control unit 39 of the main-body-side processor 42 may be integrated into, for example, one CPU.

Next, the operation of the ultrasound system 1 according to Embodiment 1 of the invention will be described. Here, for the sake of description, the operation of the ultrasound system 1 in a case in which the distance on the ultrasound diagnostic image is measured will be described below.

The ultrasound transmission and reception control unit 15 of the probe-side processor 25 controls the transmitting and receiving unit 14 such that the transducer array 11 transmits and receives ultrasonic waves on the basis of a predetermined inspection mode under the control of the probe control unit 21. Here, in the following description, for the sake of description, it is assumed that a B-mode is used as the predetermined inspection mode used for ultrasound diagnosis.

In this case, ultrasound beams are transmitted into the subject from the plurality of ultrasound transducers of the transducer array 11 according to a driving signal from the transmitting unit 12 of the transmitting and receiving unit 14 under the control of the ultrasound transmission and reception control unit 15. Ultrasound echoes from the subject, which are based on the transmitted ultrasound beams, are received by each ultrasound transducer and a reception signal which is an analog signal is output to the receiving unit 13, is amplified by the amplification unit 26, and is converted into a digital signal by the AD conversion unit 27. As a result, reception data is acquired. The beam former 28 performs a reception focusing process on the reception data to generate a sound ray signal corresponding to each frame of the ultrasound image.

The signal processing unit 16 of the image information data generation unit 19 performs attenuation correction and an envelope detection process on the sound ray signal generated by the beam former 28 of the receiving unit 13 to generate a signal which is tomographic image information related to the tissues in the subject. The image processing unit 17 of the image information data generation unit 19 performs raster conversion on the signal generated by the signal processing unit 16 and further performs various types of necessary image processing on the signal to generate an ultrasound image signal as image information data.

The ultrasound image signal generated in the image information data generation unit 19 is transmitted to the wireless communication unit 18 of the ultrasound probe 2 and is then wirelessly transmitted as a transmission signal from the wireless communication unit 18 of the ultrasound probe 2 to the wireless communication unit 32 of the diagnostic apparatus main body 3.

The transmission signal wirelessly transmitted from the wireless communication unit 18 of the ultrasound probe 2 is demodulated by the wireless communication unit 32 of the diagnostic apparatus main body 3 and is then transmitted as the ultrasound image signal to the display control unit 33 and the measurement unit 36 of the main-body-side processor 42.

The ultrasound image signal transmitted to the display control unit 33 is displayed as the ultrasound image U which is the first image on the display unit 34 of the diagnostic apparatus main body 3 under the control of the display control unit 33. In this case, as illustrated in FIG. 3, in the display unit 34, the image display region RD for displaying the ultrasound image U and the outer region RE outside the image display region RD are set, and the ultrasound image U is displayed in the image display region RD.

As described above, in a case in which the user inputs, for example, a command to measure the distance on the ultrasound image U through the operation unit 40 with the ultrasound image U displayed in the image display region RD of the display unit 34, the measurement unit 36 of the main-body-side processor 42 generates the measurement cursor C1 for measuring the distance, and the generated measurement cursor C1 is displayed on the display unit 34 through the display control unit 33. Then, as illustrated in FIG. 3, the measurement cursor C1 is displayed so as to be superimposed on the ultrasound image U.

Here, in a case in which the image display region RD of the display unit 34 is touched by the user, for example, in a case in which the measurement cursor C1 displayed so as to be superimposed on the ultrasound image U in the image display region RD is touched by the user, the second image generation unit 37 generates the second image S having a predetermined size on the basis of the touch position of the user in the image display region RD and the ultrasound image U displayed in the image display region RD.

In this case, for example, as illustrated in FIG. 4, the image display region RD is divided into four regions of the upper left region UL, the upper right region UR, the lower left region BL, and the lower right region BR which have the same size, and the image size setting unit 43 of the second image generation unit 37 sets the size of the second image S to a size that is equal to the size of the four regions in the image display region RD. Further, the image cutout unit 44 of the second image generation unit 37 cuts out the ultrasound image U of the lower left region BL touched by the finger F of the user to generate the second image S. Therefore, in the example illustrated in FIG. 4, the dimension of the second image S in the first direction D1 is half of the dimension of the image display region RD in the first direction D1, and the dimension of the second image S in the second direction D2 is half of the dimension of the image display region RD in the second direction D2. Therefore, the second image S can be displayed at a position that does not overlap the finger F of the user.

In addition, as illustrated in FIG. 4, in a case in which the measurement cursor C1 displayed so as to be superimposed on the ultrasound image U is touched by the user, the second image generation unit 37 can generate, as the second image S, an image obtained by superimposing a measurement cursor C2 that is the same as the measurement cursor C1 on the image cut out by the image cutout unit 44. Here, the measurement cursor C2 in the second image S can be moved in operative association with the measurement cursor C1 displayed so as to be superimposed on the ultrasound image U. For example, in a case in which the measurement cursor C1 displayed so as to be superimposed on the ultrasound image U is touched and moved by the user, the measurement cursor C2 in the second image S is also moved similarly to the measurement cursor C1.

Further, the second image display position determination unit 38 determines a position different from the touch position of the user on the image display region RD as the display position for displaying the second image S on the basis of the touch position of the user in the image display region RD. For example, as illustrated in FIG. 4, any one of the upper left region UL, the upper right region UR, or the lower right region BR which is different from the lower left region BL of the image display region RD touched by the finger F of the user is determined as the display position of the second image S. In the example illustrated in FIG. 4, the upper right region UR of the image display region RD is determined as the display position of the second image S. The second image display position determination unit 38 transmits information indicating the determined display position of the second image S to the second image generation unit 37.

In a case in which the second image S is generated and the display position of the second image S is determined in this way, the second image generation unit 37 displays the generated second image S at the determined display position in the image display region RD of the display unit 34 through the display control unit 33 as illustrated in FIG. 4. Further, for example, in a case in which the finger F of the user moves while touching the image display region RD and the touch position of the user moves from the lower left region BL to the upper left region UL, the second image display position determination unit 38 determines any one of the upper right region UR, the lower left region BL, or the lower right region BR different from the upper left region UL touched by the user as a new display position of the second image S, and the second image generation unit 37 displays the second image S at the newly determined display position.

Therefore, the second image S does not hinder the touch operation of the user and the touch position hidden by the finger F or the like is clearly shown to the user.

Further, the second image S is displayed on the image display region RD while the finger F of the user comes into contact with or is close to the image display region RD and the touch sensor of the operation unit 40 detects the finger F of the user, and is removed from the image display region RD in a case in which the finger F of the user is taken off from the image display region RD and the touch sensor of the operation unit 40 is not capable of detecting the finger F of the user. As such, the second image S is displayed in the image display region RD only in a case in which the user touches the image display region RD. Therefore, the ultrasound image U is effectively displayed.

As described above, according to the ultrasound system 1 of Embodiment 1, the second image generation unit 37 of the main-body-side processor 42 generates the second image S corresponding to a predetermined region which includes the touch position of the user in the ultrasound image U displayed in the image display region RD and the second image display position determination unit 38 determines a position different from the touch position of the user in the image display region RD as the display position for displaying the second image S. In a case in which the image display region RD is touched by the user, the second image S is displayed at the display position in the image display region RD. Therefore, it is possible to effectively display the ultrasound image U while enabling the user to clearly understand the touch position.

In addition, in Embodiment 1, as illustrated in FIG. 3, the image display region RD has a rectangular shape. However, the shape of the image display region RD is not limited thereto. For example, the image display region RD may have any shape such as a circular shape, an elliptical shape, or a polygonal shape. Further, the second image S is not limited to the rectangular shape and may have any shape, similarly to the image display region RD.

In addition, in Embodiment 1, the second image generation unit 37 generates the second image by cutting out the ultrasound image U of any one of the upper left region UL, the upper right region UR, the lower left region BL, or the lower right region BR into which the image display region RD is divided. However, a method for generating the second image S is not limited thereto. For example, the second image generation unit 37 may generate, as the second image S, an image obtained by enlarging the ultrasound image U of any one of the upper left region UL, the upper right region UR, the lower left region BL, or the lower right region BR, which is not illustrated. In addition, in this case, for example, the second image generation unit 37 may cut out the enlarged image into a predetermined size to generate the second image S.

In this way, it is possible to more clearly show the touch position of the user on the second image S.

Figures 6, 7:
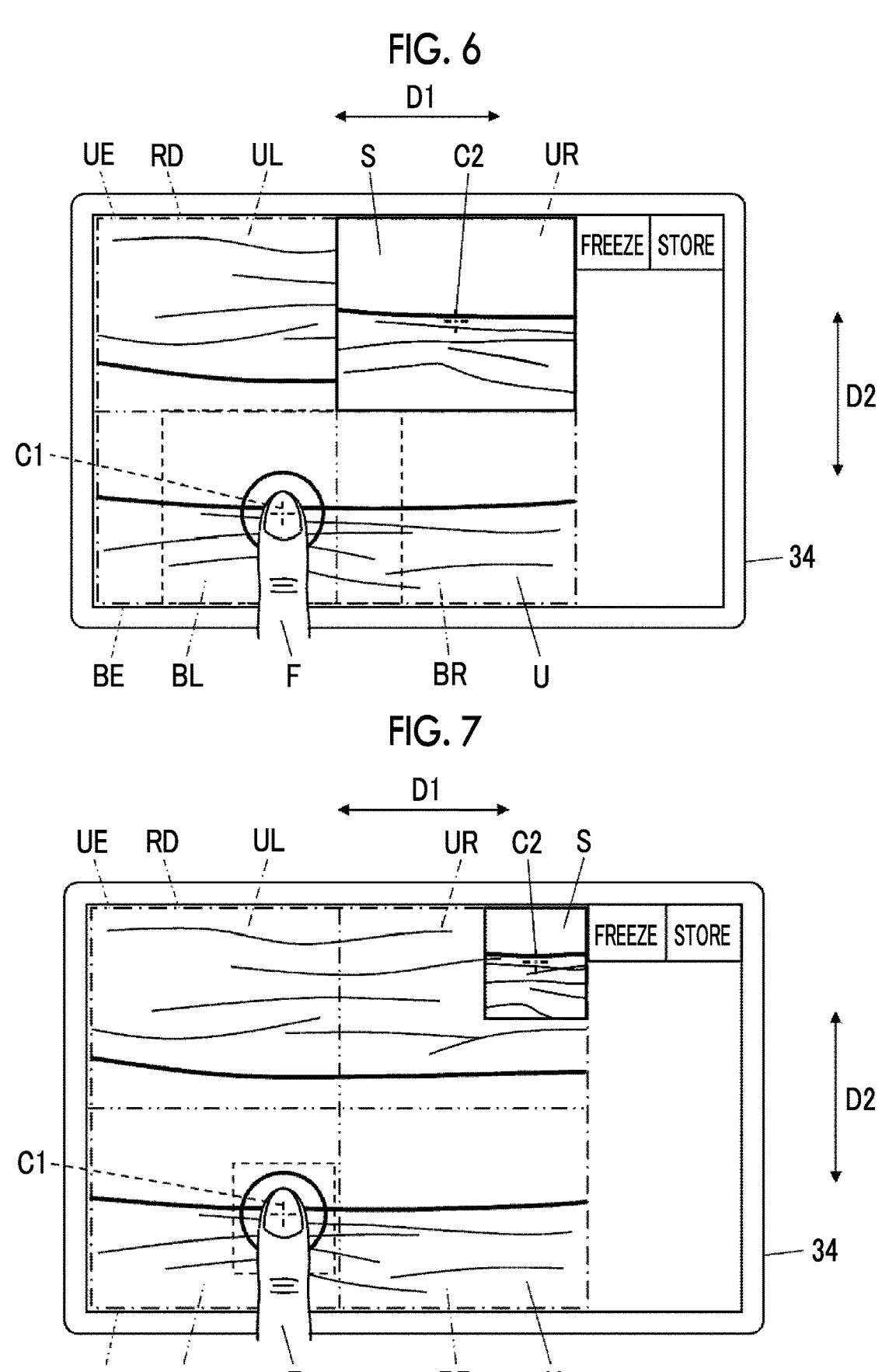
FIG. 6 is a diagram schematically illustrating a second image in a modification example of Embodiment 1 of the invention.
FIG. 7 is a diagram schematically illustrating a second image in another modification example of Embodiment 1 of the invention.

Further, for example, as illustrated in FIG. 6, the second image generation unit 37 may generate, as the second image S, an image indicating a region which has a predetermined size centered on the touch position in the ultrasound image U. In the example illustrated in FIG. 6, similarly to the second image S illustrated in FIG. 4, the dimension of the second image S in the first direction D1 is half of the dimension of the image display region RD in the first direction D1 and the dimension of the second image S in the second direction D2 is half of the dimension of the image display region RD in the second direction D2. In this case, the second image display position determination unit 38 also determines any one of the upper left region UL, the upper right region UR, or the lower right region BR different from the lower left region BL touched by the finger F of the user as the display position of the second image S.

Further, for example, as illustrated in FIG. 7, the image size setting unit 43 of the second image generation unit 37 can generate the second image S such that the dimension of the second image S in the first direction D1 is less than half of the dimension of the image display region RD in the first direction D1 and the dimension of the second image S in the second direction D2 is less than half of the dimension of the image display region RD in the second direction D2. Here, as the distance between the touch position of the user and the second image S increases, the hindrance of the second image S to the touch operation of the user is reduced. Therefore, it is desirable that the second image display position determination unit 38 determines any one of the corners of the upper left region UL, the upper right region UR, or the lower right region BR different from the lower left region BL touched by the finger F of the user as the display position of the second image S.

Figure 8:
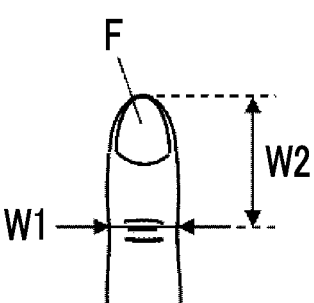
FIG. 8 is a diagram schematically illustrating a width of a finger.

In addition, the image size setting unit 43 of the second image generation unit 37 can store in advance the average value of the width of the finger based on statistical data and can set the size of the second image S to a size that is equal to or larger than the average value of the width of the finger stored in advance. For example, the image size setting unit 43 can set the dimension of the second image S in the first direction D1 to be equal to or larger than the average value of a horizontal width W1 of the distal joint of the second finger and can set the dimension of the second image S in the second direction D2 to be equal to or greater than the average value of a vertical width W2 from the tip to the distal joint of the second finger, as illustrated in FIG. 8. Here, the average value of the width of the finger based on the statistical data is the average value of the width of the finger used for the touch operation and can be stored in advance on the basis of data described in Makiko Kouchi: AIST Data on Japanese hand dimension data (2012) published by National Institute of Advanced Industrial Science and Technology. In addition, the average value of the width of the finger based on the statistical data can be appropriately set, for example, according to conditions such as race and sex touching the image display region RD of the display unit 34. As such, this setting of the size of the second image S to the size that is equal to or greater than the average value of the width of the finger makes it possible to effectively display the ultrasound image U.

Further, for example, the image size setting unit 43 can set the dimension of the second image S in the first direction D1 to be larger than the dimension of the measurement cursor C1 in the first direction D1 and can set the dimension of the second image S in the second direction D2 to be larger than the dimension of the measurement cursor C1 in the second direction D2.

In addition, for example, the image size setting unit 43 can set the size of the second image S so as to be larger than the size of the region touched by the user among the four regions of the upper left region UL, the upper right region UR, the lower left region BL, and the lower right region BR in the image display region RD. In this case, the second image display position determination unit 38 determines the display position of the second image S such that the second image S and the touch position of the user do not overlap each other.

Even in this case, the second image S can be displayed so as not to overlap the touch position of the user. Therefore, it is possible to effectively display the ultrasound image U.

Further, the image size setting unit 43 of the second image generation unit 37 can set the upper limit of the size of the second image S using the average value of the width of the finger based on the statistical data. For example, the image size setting unit 43 can set the dimension of the second image S in the first direction D1 to be equal to or less than a value obtained by subtracting the average value of the horizontal width W1 of the second finger from the dimension of the image display region RD in the first direction D1 and dividing the calculated value by 2. Furthermore, for example, the image size setting unit 43 can set the dimension of the second image S in the second direction D2 to be equal to or less than a value obtained by subtracting the average value of the vertical width W2 of the second finger from the dimension of the image display region RD in the second direction D2 and dividing the calculated value by 2. Therefore, it is possible to display the second image S at a position that does not overlap the touch position of the user, regardless of the touch position of the user.

Further, FIG. 4 illustrates a state in which the lower left region BL of the image display region RD is touched by the finger F of the user. However, in a case in which the upper left region UL and the upper right region UR of the image display region RD are touched by the finger F of the user, there is a concern that the lower left region BL and the lower right region BR of the image display region RD will be hidden by the finger F and will be difficult to visually recognize. Therefore, in a case in which the upper left region UL is touched by the finger F of the user, the second image display position determination unit 38 can determine any one of the upper right region UR or the lower right region BR different from the upper left region UL and the lower left region BL as the display position of the second image S. In a case in which the upper right region UR is touched by the finger F of the user, the second image display position determination unit 38 can determine any one of the upper left region UL or the lower left region BL different from the upper right region UR and the lower right region BR as the display position of the second image S.

As such, the second image display position determination unit 38 can determine, as the display position of the second image S, a position except a region below the touch position of the user in the second direction D2, that is, a region on a perpendicular line drawn perpendicularly to the lower edge portion BE of the image display region RD from the touch position of the user in the image display region RD.

Embodiment 2

In Embodiment 1, the image display region RD of the display unit 34 is divided into four regions. However, the invention is not limited thereto. The image display region RD may be divided into regions larger than four regions and the generation of the second image S and the determination of the display position of the second image S may be performed on the basis of the plurality of divided regions.

Figure 9:
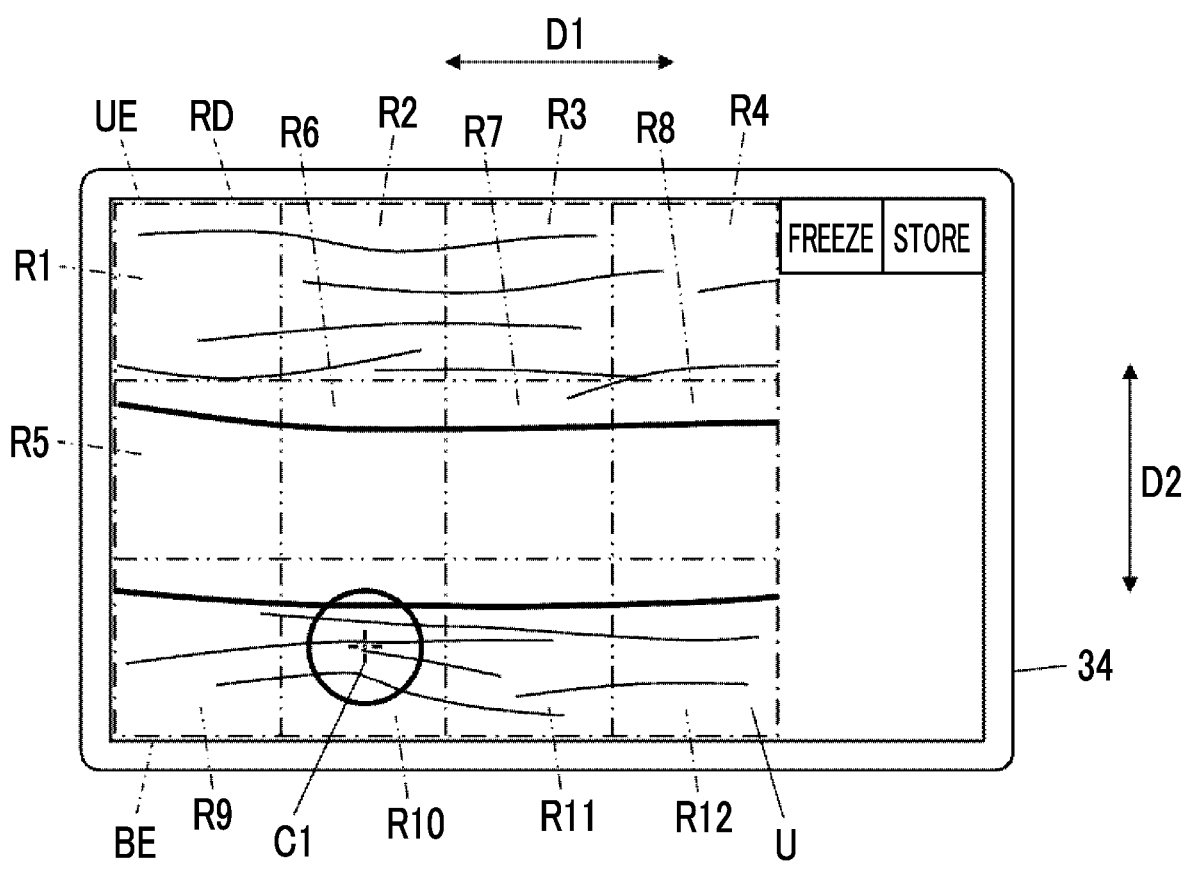
FIG. 9 is a diagram schematically illustrating an image display region in Embodiment 2 of the invention.

For example, as illustrated in FIG. 9, the image display region RD can be divided into 12 regions R1 to R12 by being divided into four regions in the first direction D1 and three regions in the second direction D2. In the example illustrated in FIG. 9, the regions R1 to R12 in the image display region RD have the same size, and the measurement cursor C1 is placed in the region R10 that is in the second column from the left in the first direction D1 and is located at the lowest position in the second direction D2.

Figures 10, 11:
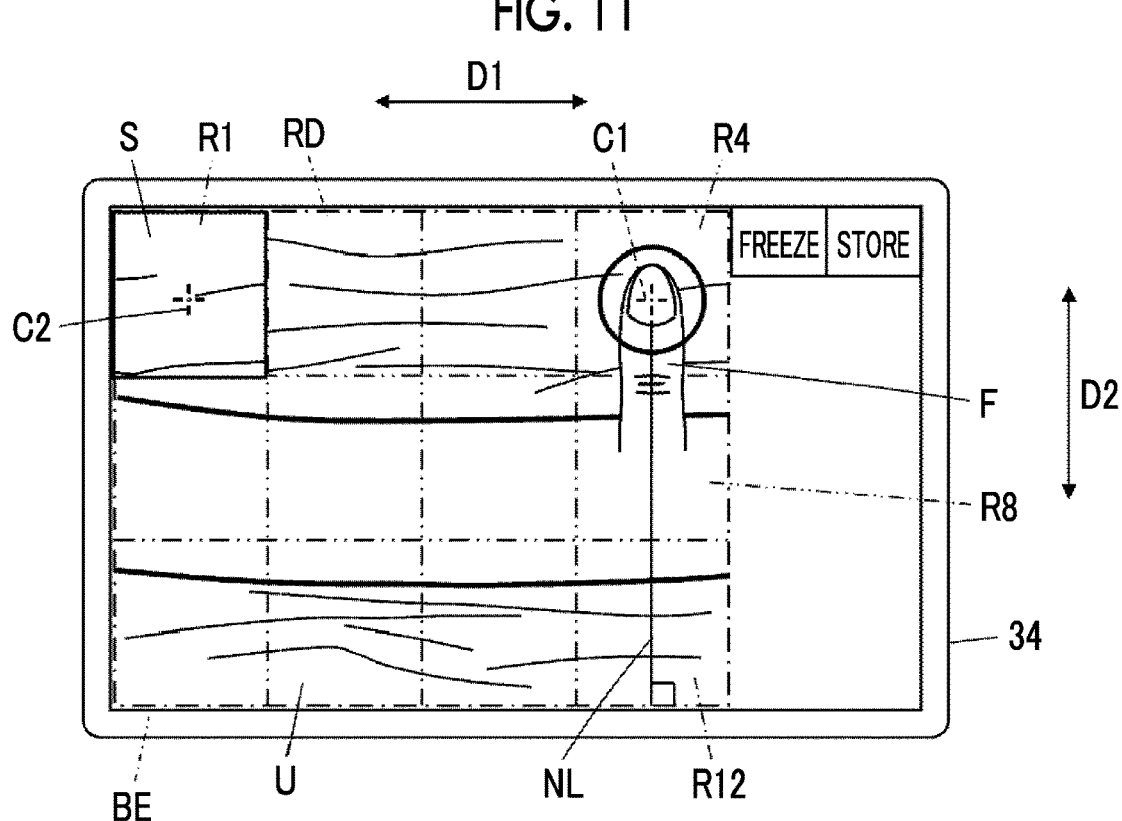
FIG. 10 is a diagram schematically illustrating a second image in Embodiment 2 of the invention.
FIG. 11 is a diagram schematically illustrating a second image in a modification example of Embodiment 2 of the invention.

In this state, in a case in which the image display region RD of the display unit 34 is touched by the user, for example, in a case in which the measurement cursor C1 displayed so as to be superimposed on the ultrasound image U in the image display region RD is touched by the user, the second image generation unit 37 generates the second image S having a predetermined size on the basis of the touch position of the user in the image display region RD and the ultrasound image U displayed in the image display region RD, as in the aspect of Embodiment 1. For example, as illustrated in FIG. 10, in a case in which the measurement cursor C1 placed in the region R10 among the 12 regions in the image display region RD is touched by the finger F of the user, the second image generation unit 37 generates, as the second image S, an image obtained by cutting out the ultrasound image U of the region R10 touched by the finger F of the user. In the example illustrated in FIG. 10, the second image S includes a measurement cursor C2 that is the same as the measurement cursor C1 displayed so as to be superimposed on the ultrasound image U.

In addition, the second image display position determination unit 38 determines a position different from the touch position of the user on the image display region RD as the display position for displaying the second image S on the basis of the touch position of the user in the image display region RD, as in the aspect of Embodiment 1. For example, as illustrated in FIG. 10, among the 12 regions in the image display region RD, any one of 11 regions different from the region R10 touched by the finger F of the user is determined as the display position of the second image S. In the example illustrated in FIG. 10, among the 12 regions in the image display region RD, the region R4 located at the upper right corner of the image display region RD is determined as the display position of the second image S.

The second image display position determination unit 38 transmits information indicating the determined display position of the second image S to the second image generation unit 37. The second image generation unit 37 displays the generated second image S at the determined display position in the image display region RD of the display unit 34 through the display control unit 33, as illustrated in FIG. 10.

As described above, even in a case in which the image display region RD of the display unit 34 is divided into a plurality of regions larger than four regions, as in the aspect of Embodiment 1, the second image generation unit 37 of the main-body-side processor 42 generates the second image S corresponding to a predetermined region which includes the touch position of the user in the ultrasound image U displayed in the image display region RD, and the second image display position determination unit 38 determines a position different from the touch position of the user in the image display region RD as the display position for displaying the second image S. In a case in which the image display region RD is touched by the user, the second image S is displayed at the display position in the image display region RD. Therefore, it is possible to effectively display the ultrasound image U while enabling the user to clearly understand the touch position.

In addition, the various aspects illustrated in Embodiment 1 can be applied to the aspect of Embodiment 2.

For example, the second image generation unit 37 can generate, as the second image S, an image obtained by enlarging the ultrasound image U of the region touched by the user among the 12 regions in the image display region RD.

Further, the image size setting unit 43 of the second image generation unit 37 can store in advance the average value of the width of the finger based on statistical data and can set the upper limit of the dimension of the second image S in the first direction D1 and the upper limit of the dimension of the second image S in the second direction D2 on the basis of the average value of the width of the finger, as in the aspect of Embodiment 1.

Furthermore, the second image generation unit 37 can set the size of the second image S to a size that is equal to or greater than the average value of the width of the finger stored in advance.

In addition, in Embodiment 2, the second image display position determination unit 38 determines, as the display position of the second image S, a region that is different from the region touched by the user among the 12 regions in the image display region RD. For example, a region that is farthest from the touch position of the user can be determined as the display position of the second image S. In the example illustrated in FIG. 10, the second image S is displayed in the region R4 farthest from the region R10 which is the touch position of the user among the regions R1 to R12 in the image display region RD.

Further, for example, in the example illustrated in FIG. 10, among the regions R1 to R12 in the image display region RD, a position except five regions R5, R6, R7, R9, and R11 adjacent to the region R10 touched by the finger F of the user, that is, any one of six regions R1 to R4, R8, and R12 can be set as the display position of the second image S. As such, the second image display position determination unit 38 determines, as the display position of the second image S, a position except the region touched by the user and the regions adjacent to the region touched by the user. Therefore, it is possible to determine a position away from the touch position of the user as the display position of the second image S while always displaying the ultrasound image U around the touch position of the user. As a result, it is possible to efficiently display the ultrasound image U.

In addition, in a case in which one of the 12 regions in the image display region RD is touched by the user, the second image display position determination unit 38 can determine, as the display position of the second image S, any one of the positions except a region below the region touched by the user in the second direction D2, that is, a region on a perpendicular line drawn perpendicularly to the lower edge portion BE of the image display region RD from the touch position of the user. For example, as illustrated in FIG. 11, in a case in which the region R4 is touched by the user, the second image display position determination unit 38 determines, as the display position of the second image S, any one of nine regions except three regions R4, R8, and R12 on a perpendicular line NL drawn perpendicularly to the lower edge portion BE of the image display region RD from the touch position of the user. In FIG. 11, the second image S is displayed in the region R1.

Figures 12, 13:
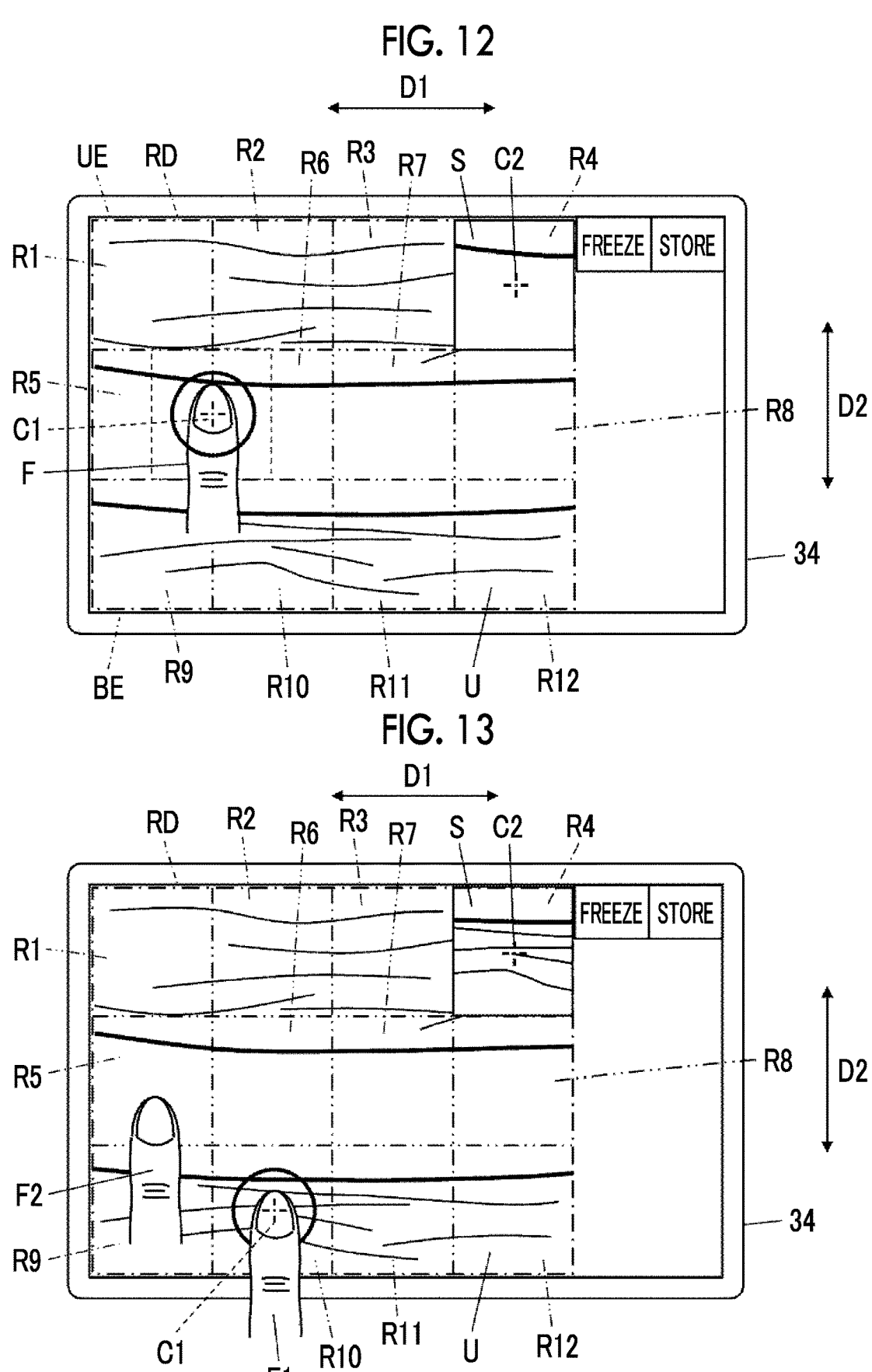
FIG. 12 is a diagram schematically illustrating a second image in another modification example of Embodiment 2 of the invention.
FIG. 13 is a diagram schematically illustrating a second image in Embodiment 3 of the invention.

Further, for example, as illustrated in FIG. 12, in a case in which the finger F of the user touches a position across the region R5 that is in the leftmost column in the first direction D1 and is located in the middle in the second direction D2 and the region R6 that is adjacent to the region R5 in the first direction D1 among the regions R1 to R12 in the image display region RD, the second image display position determination unit 38 can determine, as the display position of the second image S, a position different from the regions R5 and R6, that is, any one of the regions R1 to R4 and R7 to R12. In addition, in this case, the second image display position determination unit 38 can determine, as the display position of the second image S, a position except the region R5, the region R6, the region R9 located below the region R5, and the region R10 located below the region R6, that is, any one of the regions R1 to R4, R7, R8, R11, and R12.

As such, in a case in which the finger F of the user touches across a plurality of regions among the plurality of regions in the image display region RD, the second image display position determination unit 38 can determine, as the display position of the second image S, a position different from the plurality of regions touched by the finger F of the user. Further, the second image display position determination unit 38 can determine, as the display position of the second image S, a position except regions located below the plurality of regions touched by the finger F of the user in the second direction D2. Therefore, it is possible to determine a position away from the touch position of the user as the display position of the second image S while always displaying the ultrasound image U around the touch position of the user. As a result, it is possible to efficiently display the ultrasound image U.

In addition, as illustrated in FIG. 12, the second image generation unit 37 can generate, as the second image S, the ultrasound image U of the region that has a predetermined size centered on the touch position of the user as in the aspect described in Embodiment 1. In this case, as illustrated in FIG. 12, the second image generation unit 37 can generate the second image S including the touch position of the user even though the finger F of the user touches across a plurality of regions in the image display region RD.

Further, in Embodiments 1 and 2, the image display region RD of the display unit 34 is divided into a plurality of regions. However, the image display region RD may not be divided into a plurality of regions, the second image S may be generated, and the display position of the second image S may be determined. In this case, the second image generation unit 37 can generate, as the second image S, an image corresponding a region that includes the touch position of the user and has a predetermined size in the ultrasound image U, as in the aspect of Embodiment 1 and the aspect of Embodiment 2. In addition, the second image display position determination unit 38 can determine, as the display position of the second image S, a position different from the touch position of the user, for example, a position farthest from the touch position of the user, as in the aspect of Embodiment 1 and the aspect of Embodiment 2.

Embodiment 3

In Embodiment 1 and Embodiment 2, the number of touch positions of the user in the image display region RD is one. However, the invention can also be applied to a case in which there are a plurality of touch positions in the image display region RD.

For example, it is assumed that, as illustrated in FIG. 13, among the regions R1 to R12 in the image display region RD, the measurement cursor C1 is placed in the region R10, the finger F1 of the user touches the region R10, and a finger F2 of the user touches the region R5. In this case, for example, the image cutout unit 44 of the second image generation unit 37 determines that the input operation in the region R10 in which the measurement cursor C1 is placed is more useful than the input operation in the region R5 in which the measurement cursor C1 is not placed and cuts out the ultrasound image U of the region R10, in which the measurement cursor C1 is placed, of the regions R5 and R10 touched by the user to generate the second image S. In addition, for example, in a case in which the user touches the region R2 and the region R5, the image cutout unit 44 determines that the input operation in the region R5 close to the region R10 in which the measurement cursor C1 is placed is more useful than the input operation in the region R2 far from the measurement cursor C1 and cuts out the ultrasound image U of the region R5 to generate the second image S, which is not illustrated.

As such, in a case in which there are a plurality of touch positions in the image display region RD and an operable target, such as the measurement cursor C1, is placed in the image display region RD, the image cutout unit 44 of the second image generation unit 37 cuts out the ultrasound image U of a region including a touch position close to the operable target, such as the measurement cursor C1, among the plurality of touch positions to generate the second image S. Therefore, it is possible to generate the ultrasound image U of the region in which the input operation is more useful as the second image S.

Further, for example, as illustrated in FIG. 13, in a case in which, among the regions R1 to R12 in the image display region RD, the region R10 is touched by the finger F1 of the user and the region R5 is touched by the finger F2 of the user, the second image display position determination unit 38 of the main-body-side processor 42 can determine any one of the regions R1 to R4, R6 to R8, R9, R11 and R12 different from the regions R5 and R10 touched by the user as the display position of the second image S. Here, it is desirable that a position which is away from the touch position of the user so as not to hinder the touch operation of the user is set as the display position of the second image S. Therefore, it is desirable that, for example, as illustrated in FIG. 13, the second image display position determination unit 38 determines the region R4 which is farthest from the regions R5 and R10 touched by the user as the display position of the second image S.

As such, in a case in which there are a plurality of touch positions in the image display region RD, the second image display position determination unit 38 can determine a position different from the plurality of touch positions in the image display region RD as the display position of the second image S. In particular, it is desirable that the second image display position determination unit 38 determines a position which is farthest from the plurality of touch positions in the image display region RD as the display position of the second image S.

As described above, according to the ultrasound system of Embodiment 3, even in a case in which there are a plurality of touch positions in the image display region RD of the display unit 34, as in the aspect of Embodiment 1 and the aspect of Embodiment 2, the second image generation unit 37 of the main-body-side processor 42 generates the second image S corresponding to a predetermined region including the touch position of the user in the ultrasound image U displayed in the image display region RD, and the second image display position determination unit 38 determines a position different from the touch position of the user in the image display region RD as the display position for displaying the second image S. In a case in which the image display region RD is touched by the user, the second image S is displayed at the display position in the image display region RD. Therefore, it is possible to effectively display the ultrasound image U while enabling the user to clearly understand the touch position.

Even in a case in which there are a plurality of touch positions in the image display region RD, various aspects of Embodiments 1 and 2 can be applied. For example, the second image display position determination unit 38 can determine a position except the region that is located below the touch position of the user in the second direction D2 as the display position of the second image S. For example, in the example illustrated in FIG. 13, the second image display position determination unit 38 can determine a region different from the region R5, the region R9 located below the region R5, and the region R10 as the display position of the second image S.

Embodiment 4

In Embodiments 1 to 3, the image size setting unit 43 of the second image generation unit 37 sets the size of the second image S to a predetermined size. However, the size of the second image S may be set on the basis of the width of the finger F of the user who actually touches the image display region RD. An ultrasound system according to Embodiment 4 is different from the ultrasound system 1 according to Embodiment 1 illustrated in FIG. 1 in that it comprises a second image generation unit 37A illustrated in FIG. 14 instead of the second image generation unit 37 of the diagnostic apparatus main body 3.

Figure 14:
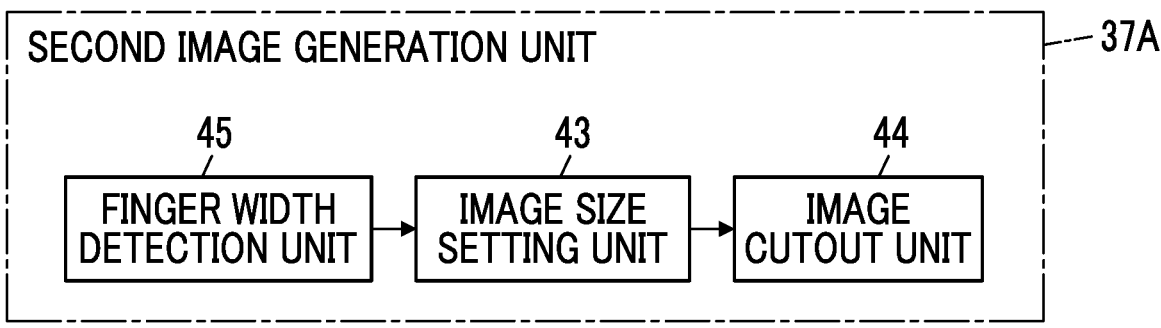
FIG. 14 is a block diagram illustrating an internal configuration of a second image generation unit in Embodiment 4 of the invention.

As illustrated in FIG. 14, the second image generation unit 37A according to Embodiment 4 is different from the second image generation unit 37 according to Embodiment 1 illustrated in FIG. 5 in that it further includes a finger width detection unit 45 and the finger width detection unit 45 is connected to the image size setting unit 43.

The finger width detection unit 45 of the second image generation unit 37A detects the width of the finger F of the user who touches the image display region RD in a case in which the finger F of the user touches the image display region RD. In this case, first, in a case in which the finger F of the user touches the image display region RD, the touch sensor of the operation unit 40 detects which portion of the image display region RD is touched by the finger F of the user and transmits information indicating the region touched by the finger F of the user in the image display region RD to the main body control unit 39. The finger width detection unit 45 receives the information indicating the region touched by the finger F of the user in the image display region RD from the main body control unit 39 and detects the width of the finger F of the user on the basis of the information.

Figure 15:
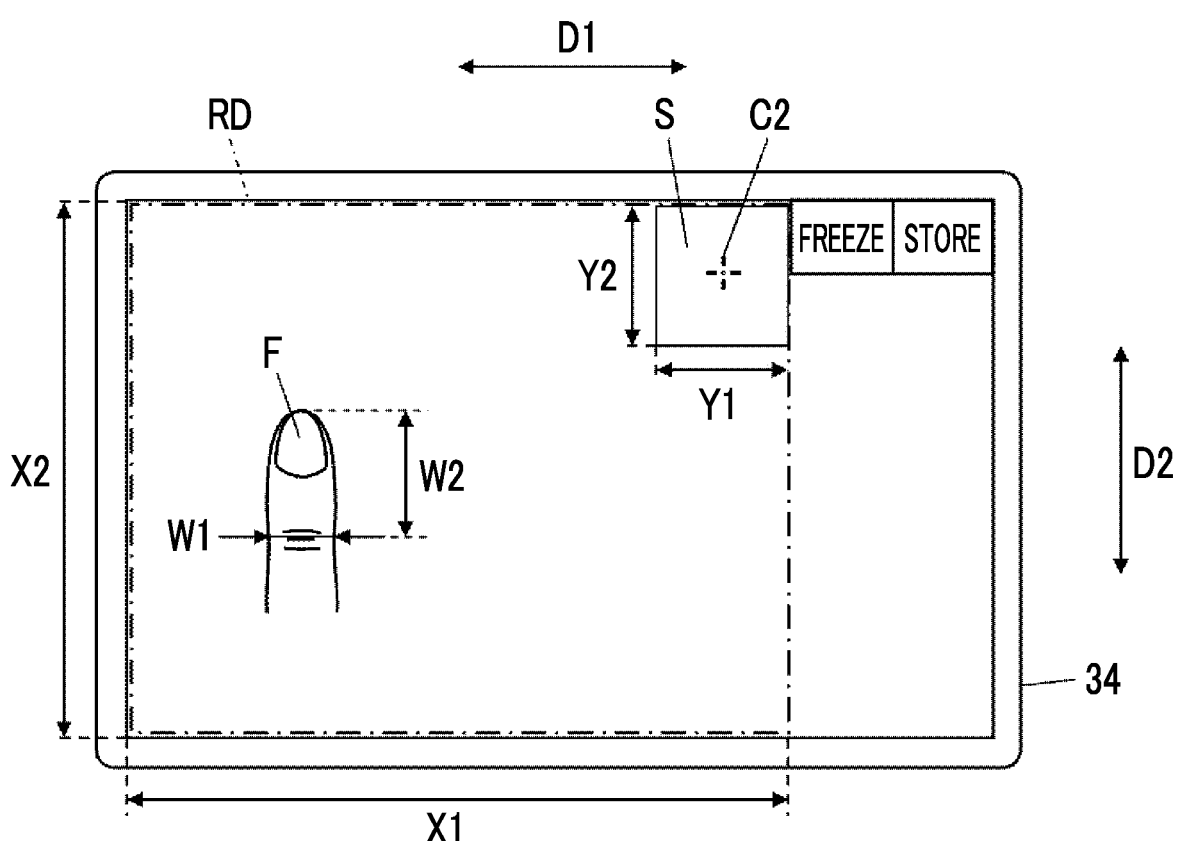
FIG. 15 is a diagram schematically illustrating a second image in Embodiment 4 of the invention.

The image size setting unit 43 of the second image generation unit 37A sets the size of the second image S on the basis of the width of the finger F of the user detected by the finger width detection unit 45. For example, it is assumed that the dimension of the image display region RD in the first direction D1 is X1, the horizontal width of the distal joint of the second finger in the fingers F of the user detected by the finger width detection unit 45 is W1, and k is an integer equal to or greater than 2 as illustrated in FIG. 15. For example, in a case in which the horizontal width W1 of the finger of the user is less than half of the dimension X1 of the image display region RD in the first direction D1, the image size setting unit 43 can set the dimension Y1 of the second image S in the first direction D1, using the following Expression (1).

$$Y1 = (X1 - 2 \times W1)/k \qquad (1)$$

Therefore, it is possible to display the second image S so as not to overlap the finger F of the user in the first direction D1. Here, in practice, the ultrasound image U is displayed in the image display region RD. However, the ultrasound image U is omitted in FIG. 15 for the sake of description.

Further, for example, in a case in which the horizontal width W1 of the finger of the user is greater than half of the dimension X1 of the image display region RD in the first direction D1, the image size setting unit 43 can set the integer k that is equal to or greater than 2 and satisfies the following Expression (2) and can set the dimension Y1 of the second image S in the first direction D1 from the following Expression (2).

$$Y1 = (2 \times W1 - X1)/k \qquad (2)$$

This setting of the dimension Y1 of the second image S in the first direction D1 using Expression (2) makes it possible to display the second image S at a position that does not overlap the touch position of the user.

In addition, for example, in a case in which the horizontal width W1 of the finger F of the user detected by the finger width detection unit 45 is greater than half of the dimension X1 of the image display region RD in the first direction D1, the image size setting unit 43 may determine that the palm or the like different from the finger of the user has come into contact with the image display region RD and an error occurs, without performing the calculation using Expression (2). In this case, for example, the image size setting unit 43 can set the size of the second image S to a predetermined size as in the aspect of Embodiment 1 and the aspect of Embodiment 2.

In addition, for example, it is assumed that the dimension of the image display region RD in the second direction D2 is X2, the vertical width from the tip to the distal joint of the second finger in the fingers F of the user detected by the finger width detection unit 45 is W2, and k is an integer equal to or greater than 2 as illustrated in FIG. 15. For example, in a case in which the vertical width W2 of the finger of the user is less than half of the dimension X2 of the image display region RD in the second direction D2, the image size setting unit 43 can set the dimension Y2 of the second image S in the second direction D2 using the following Expression (3).

$$Y2 = (X2 - 2 \times W2)/k \qquad (3)$$

Therefore, it is possible to display the second image S so as not to overlap the finger F of the user in the second direction D2.

Further, for example, in a case in which the vertical width W2 of the finger of the user is greater than half of the dimension X2 of the image display region RD in the second direction D2, the image size setting unit 43 can set the integer k that is equal to or greater than 2 and satisfies the following Expression (4) and can set the dimension Y2 of the second image S in the second direction D2 from the following Expression (4).

$$Y2 = (2 \times W2 - X2)/k \qquad (4)$$

This setting of the dimension Y2 of the second image S in the second direction D2 using Expression (4) makes it possible to display the second image S at a position that does not overlap the touch position of the user.

In addition, for example, in a case in which the vertical width W2 of the finger F of the user detected by the finger width detection unit 45 is greater than half of the dimension X2 of the image display region RD in the second direction D2, the image size setting unit 43 may determine that the palm or the like different from the finger of the user has come into contact with the image display region RD and an error occurs, without performing the calculation using Expression (4). In this case, for example, the image size setting unit 43 can set the size of the second image S to a predetermined size as in the aspect of Embodiment 1 and the aspect of Embodiment 2.

The image cutout unit 44 of the second image generation unit 37A cuts out an image of a region which has the size of the second image S set by the image size setting unit 43 and includes the touch position of the user in the ultrasound image U displayed in the image display region RD to generate the second image S.

The second image display position determination unit 38 of the main-body-side processor 42 determines a position different from the touch position of the finger F of the user as the display position of the second image S generated by the second image generation unit 37A. For example, the second image display position determination unit 38 determines a position which does not overlap the touch position of the user and which is farthest from the touch position of the user, as the display position second image S, using an image analysis method or the like. In the example illustrated in FIG. 15, the upper right corner of the image display region RD is determined as the display position of the second image S.

As described above, according to the ultrasound system of Embodiment 4, the second image generation unit 37 includes the finger width detection unit 45 that detects the width of the finger of the user who touches the image display region RD of the display unit 34 and the image size setting unit 43 of the second image generation unit 37A sets the size of the second image S on the basis of the width of the finger F of the user detected by the finger width detection unit 45. Therefore, it is possible to display the second image S so as not to further overlap the finger F of the user and to more effectively display the ultrasound image U.

A method for setting the size of the second image S in the image size setting unit 43 of the second image generation unit 37A is not limited to the method using Expressions (1)

to (4). For example, the image size setting unit 43 can set, as the dimension Y1 of the second image S in the first direction D1, a value obtained by subtracting the horizontal width W1 of the finger F of the user detected by the finger width detection unit 45 from the dimension X1 of the image display region RD in the first direction D1 and dividing the calculated value by 2. That is, the dimension Y1 of the second image S in the first direction D1 can be set using the following Expression (5).

$$Y1 = (X1 - W1)/2 \qquad (5)$$

For the second direction D2, similarly, the image size setting unit 43 can set, as the dimension Y2 of the second image S in the second direction D2, a value obtained by subtracting the vertical width W2 of the finger F of the user detected by the finger width detection unit 45 from the dimension X2 of the image display region RD in the second direction D2 and dividing the calculated value by 2. That is, the dimension Y2 of the second image S in the second direction D2 can be set using the following Expression (6).

$$Y2 = (X2 - W2)/2 \qquad (6)$$

Even in a case in which the size of the second image S is set using Expressions (5) and (6), it is possible to display the second image S at a position that does not overlap the touch position of the user, regardless of the touch position of the user in the image display region RD.

Further, for example, the image size setting unit 43 can set a natural number n1 that is equal to or greater than 2 and is less than the value obtained by dividing the dimension X1 of the image display region RD in the first direction D1 by the horizontal width W1 of the finger F of the user and can set a value obtained by further dividing the dimension X1 of the image display region RD in the first direction D1 by the natural number n1 as the dimension Y1 of the second image S in the first direction D1. In this case, the image size setting unit 43 sets the value of the natural number n1 in consideration of the touch position of the user in the first direction D1, which makes it possible to display the second image S at a position that does not overlap the touch position of the user in the first direction D1. For the second direction D2, similarly, the image size setting unit 43 can set a natural number n2 that is equal to or greater than 2 and is less than the value obtained by dividing the dimension X2 of the image display region RD in the second direction D2 by the vertical width W2 of the finger F of the user and can set a value obtained by further dividing the dimension X2 of the image display region RD in the second direction D2 by the natural number n2 as the dimension Y2 of the second image S in the second direction D2. Similarly to the case in which the dimension Y1 of the second image S in the first direction D1 is set, the image size setting unit 43 sets the value of the natural number n2 in consideration of the touch position of the user in the second direction D2, which makes it possible to display the second image S at a position that does not overlap the touch position of the user in the second direction D2.

Embodiment 5

Figure 16:
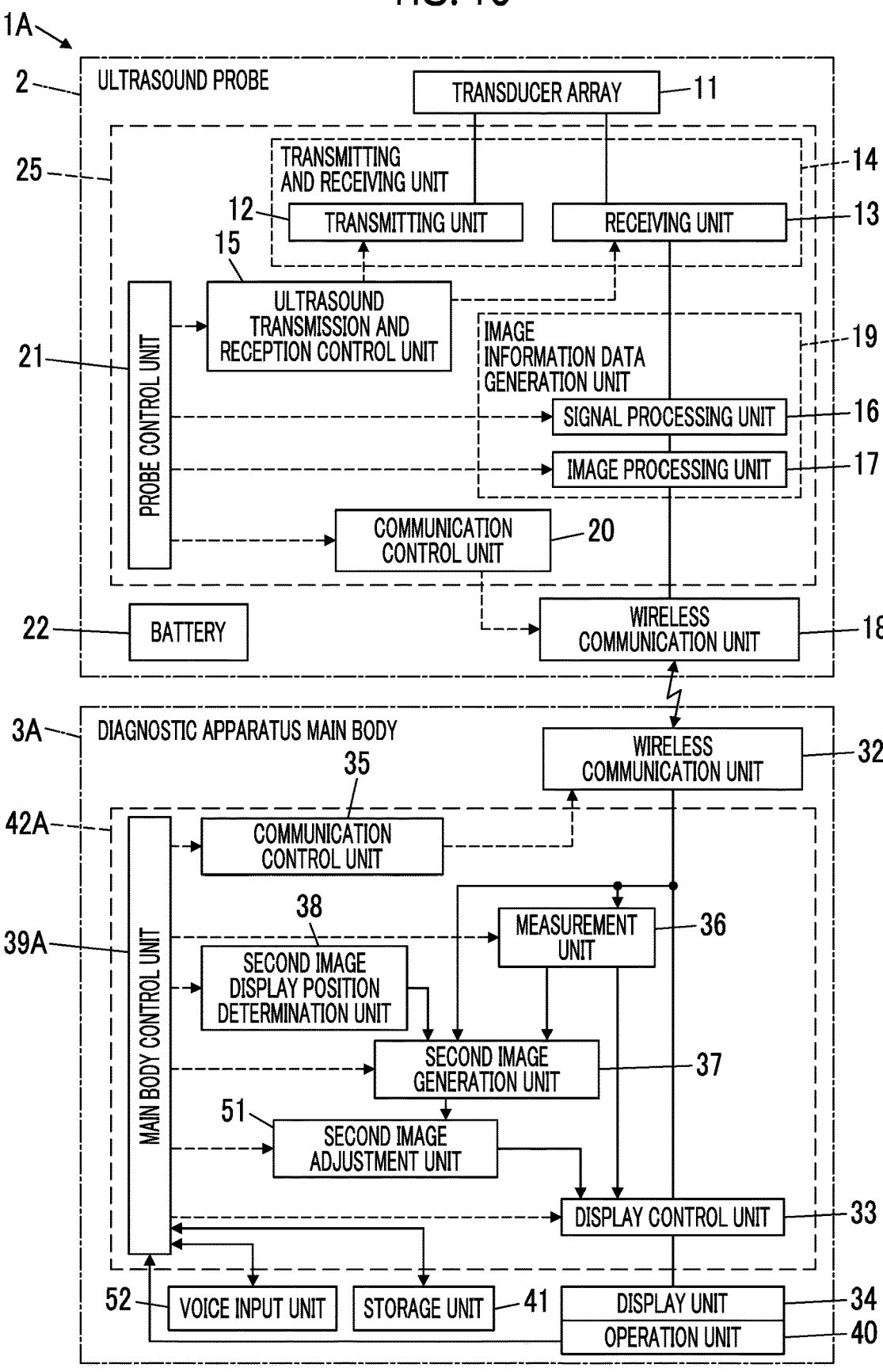
FIG. 16 is a block diagram illustrating a configuration of an ultrasound system according to Embodiment 5 of the invention.

FIG. 16 illustrates the configuration of an ultrasound system 1A according to Embodiment 5. The ultrasound system 1A according to Embodiment 5 is different from the ultrasound system 1 according to Embodiment 1 illustrated in FIG. 1 in that it comprises a diagnostic apparatus main body 3A instead of the diagnostic apparatus main body 3. The diagnostic apparatus main body 3A according to Embodiment 5 is different from the diagnostic apparatus main body 3 according to Embodiment 1 illustrated in FIG. 1 in that a main body control unit 39A is provided instead of the main body control unit 39 and a second image adjustment unit 51 and a voice input unit 52 are added.

In the diagnostic apparatus main body 3A, the second image adjustment unit 51 is connected to the second image generation unit 37, and the display control unit 33 is connected to the second image adjustment unit 51. Further, the main body control unit 39A is connected to the display control unit 33, the communication control unit 35, the measurement unit 36, the second image generation unit 37, the second image display position determination unit 38, the operation unit 40, the storage unit 41, and the second image adjustment unit 51, and the voice input unit 52 is connected to the main body control unit 39A. The main body control unit 39A and the voice input unit 52 are connected such that information can be bidirectionally transmitted and received.

Furthermore, a main-body-side processor 42A is configured by the display control unit 33, the communication control unit 35, the measurement unit 36, the second image generation unit 37, the second image display position determination unit 38, the main body control unit 39A, and the second image adjustment unit 51.

The voice input unit 52 of the diagnostic apparatus main body 3A is for performing an input operation using the user's voice or the like and is configured by, for example, a circuit including a microphone that converts the voice around the diagnostic apparatus main body 3A into voice data which is an electric signal. The voice input unit 52 recognizes the voice data obtained by the microphone and transmits command information represented by the user's voice or the like to the main body control unit 39A.

The second image adjustment unit 51 of the main-body-side processor 42A changes at least one of the size of the second image S generated by the second image generation unit 37 or the display position of the second image S determined by the second image display position determination unit 38 according to the input operation of the user through, for example, the voice input unit 52 and displays the second image S in the image display region RD of the display unit 34.

For example, in a case in which the user issues a voice command "down" while touching the image display region RD with the finger, command information represented by the user's voice is input to the second image adjustment unit 51 through the voice input unit 52 and the main body control unit 39A. The second image adjustment unit 51 moves the position of the second image S currently displayed in the image display region RD to the lower side of the image display region RD while avoiding the touch position of the user on the basis of the command information. In addition, for example, in a case in which the user issues a voice command "3 mm right", the second image adjustment unit 51 moves the position of the second image S currently displayed in the image display region RD by 3 mm in the right direction.

Further, for example, in a case in which the user issues a voice command "enlarge", the second image adjustment unit 51 enlarges and displays the second image S such that the second image S does not overlap the finger of the user.

The voice operation may be performed by the input operation of the user through the operation unit 40. For example, in a case in which the user taps the image display region RD only once with the finger, the second image adjustment unit 51 can enlarge and display the second image S such that the second image S does not overlap the finger of the user.

As described above, according to the ultrasound system 1A of Embodiment 5, it is possible to adjust the size and position of the second image S in a state in which the second image S is displayed in the image display region RD of the display unit 34. Therefore, it is possible to improve convenience in ultrasound diagnosis.

Embodiment 6

Figure 17:
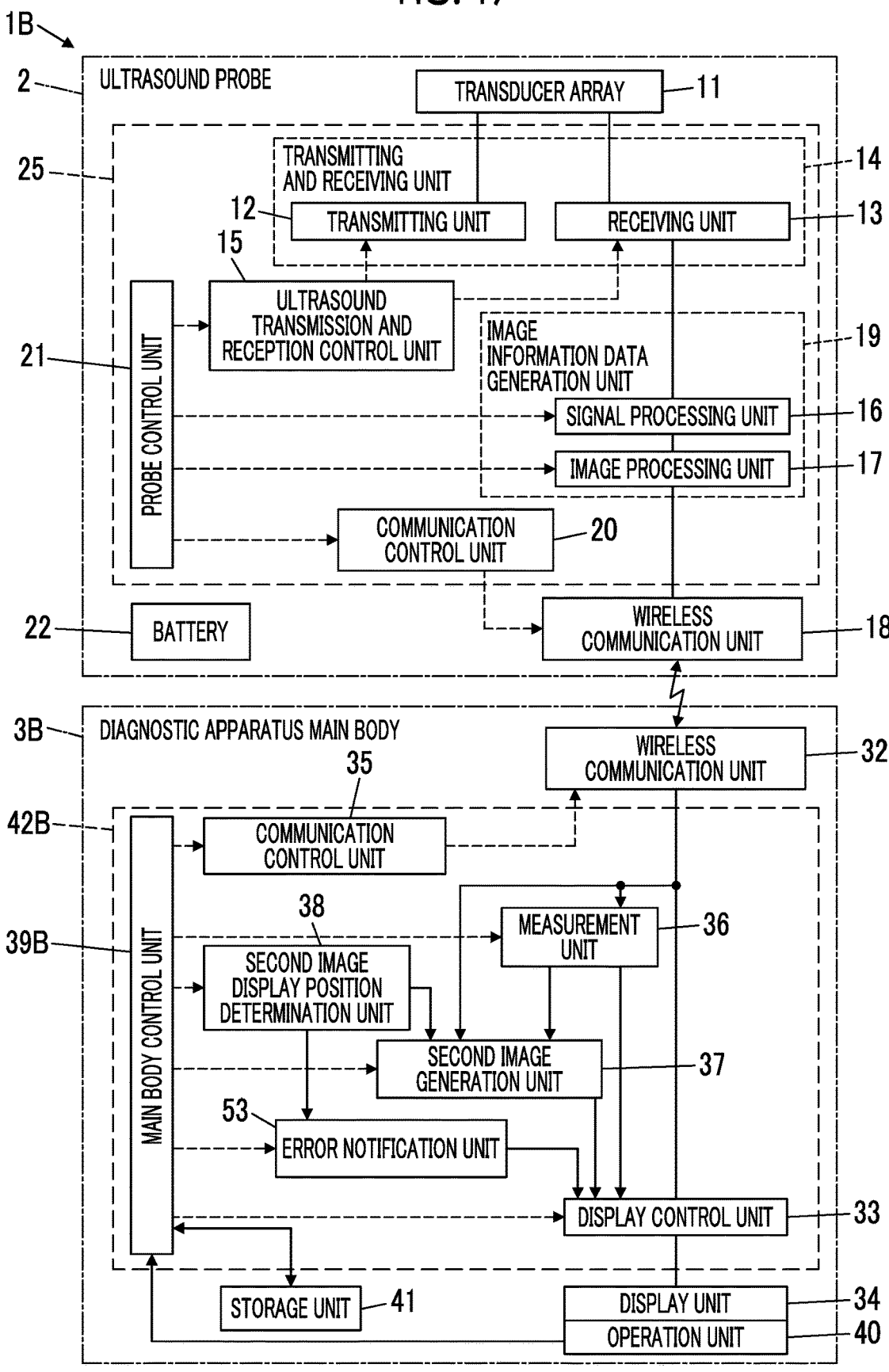
FIG. 17 is a block diagram illustrating a configuration of an ultrasound system according to Embodiment 6 of the invention.

FIG. 17 illustrates the configuration of an ultrasound system 1B according to Embodiment 6. The ultrasound system 1B according to Embodiment 6 is different from the ultrasound system 1 according to Embodiment 1 illustrated in FIG. 1 in that it comprises a diagnostic apparatus main body 3B instead of the diagnostic apparatus main body 3. The diagnostic apparatus main body 3B according to Embodiment 6 is different from the diagnostic apparatus main body 3 according to Embodiment 1 illustrated in FIG. 1 in that a main body control unit 39B is provided instead of the main body control unit 39 and an error notification unit 53 is added.

In the diagnostic apparatus main body 3B, the error notification unit 53 is connected to the second image display position determination unit 38, and the display control unit 33 is connected to the error notification unit 53. Further, the main body control unit 39B is connected to the display control unit 33, the communication control unit 35, the measurement unit 36, the second image generation unit 37, the second image display position determination unit 38, the operation unit 40, the storage unit 41, and the error notification unit 53. Furthermore, a main-body-side processor 42B is configured by the display control unit 33, the communication control unit 35, the measurement unit 36, the second image generation unit 37, the second image display position determination unit 38, the main body control unit 39, and the error notification unit 53.

In a case in which the second image display position determination unit 38 is not capable of determining the display position of the second image S, the error notification unit 53 of the main-body-side processor 42B notifies the user that an error has occurred. For example, in a case in which it is difficult to ensure a sufficient space to display the second image S having a predetermined size in the image display region RD due to the touch position of the user, the error notification unit 53 can display a message indicating that it is difficult to ensure a sufficient space to display the second image S on the image display region RD on the display unit 34 through the display control unit 33. In addition, for example, the error notification unit 53 may display a message that prompts the user to move the position of the finger F touching the image display region RD on the display unit 34.

Here, for example, a text and an image can be used as the message displayed to the user on the display unit 34 by the error notification unit 53. Further, a voice generation unit that generates a voice may be provided in the diagnostic apparatus main body 3B and the error notification unit 53 may issue a message to the user using the voice through the voice generation unit, which is not illustrated.

As described above, according to the ultrasound system 1B of Embodiment 6, in a case in which the second image display position determination unit 38 is not capable of determining the display position of the second image S, the error notification unit 53 notifies the user that an error has occurred. Therefore, it is possible to alert the user such that the second image S is displayed in the image display region RD.

Embodiment 7

Figure 18:
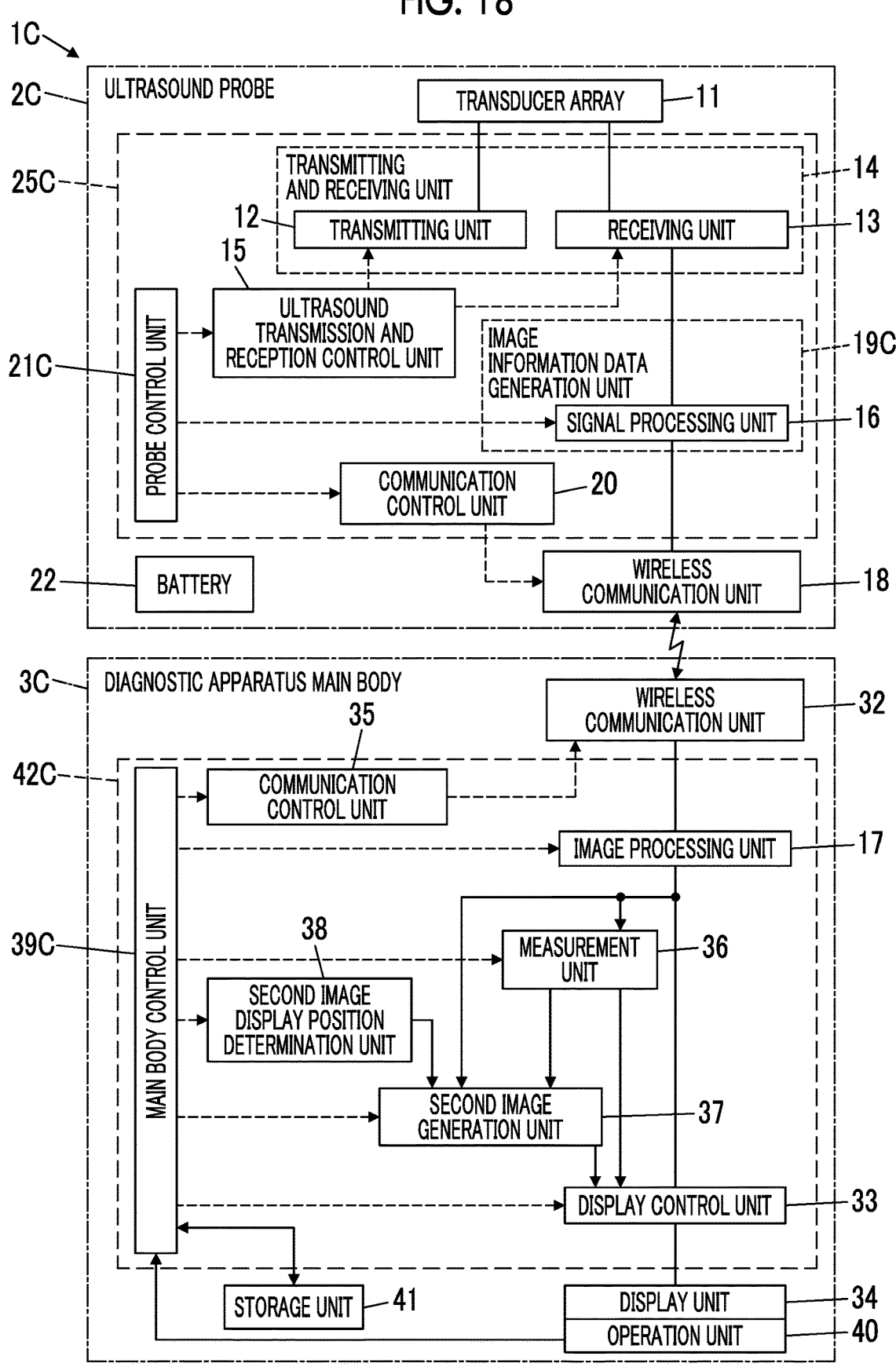
FIG. 18 is a block diagram illustrating a configuration of an ultrasound system according to Embodiment 7 of the invention.

FIG. 18 illustrates the configuration of an ultrasound system 1C according to Embodiment 7. The ultrasound system 1C comprises an ultrasound probe 2C and a diagnostic apparatus main body 3C. The ultrasound probe 2C is different from the ultrasound probe 2 according to Embodiment 1 illustrated in FIG. 1 in that a probe control unit 21C is provided instead of the probe control unit 21 and the image processing unit 17 is removed.

In the ultrasound probe 2C, the wireless communication unit 18 is directly connected to the signal processing unit 16, and an image information data generation unit 19C is configured by the signal processing unit 16. The probe control unit 21C is connected to the ultrasound transmission and reception control unit 15, the signal processing unit 16, and the communication control unit 20. In addition, a probe-side processor 25C is configured by the transmitting and receiving unit 14, the ultrasound transmission and reception control unit 15, the image information data generation unit 19C, the communication control unit 20, and the probe control unit 21C.

Further, the diagnostic apparatus main body 3C of the ultrasound system 1C is different from the diagnostic apparatus main body 3 according to Embodiment 1 illustrated in FIG. 1 in that it comprises a main body control unit 39C instead of the main body control unit 39 and comprises the image processing unit 17 between the wireless communication unit 32 and the display control unit 33. The image processing unit 17 in the diagnostic apparatus main body 3C is the same as the image processing unit 17 in the ultrasound probe 2 illustrated in FIG. 1.

In the diagnostic apparatus main body 3C, the image processing unit 17 is connected to the wireless communication unit 32, and the display control unit 33 is connected to the image processing unit 17. Further, the main body control unit 39C is connected to the image processing unit 17, the display control unit 33, the communication control unit 35, the measurement unit 36, the second image generation unit 37, the second image display position determination unit 38, the operation unit 40, and the storage unit 41.

Furthermore, a main-body-side processor 42C is configured by the image processing unit 17, the display control unit 33, the communication control unit 35, the measurement unit 36, the second image generation unit 37, the second image display position determination unit 38, and the main body control unit 39C.

The signal processing unit 16 of the image information data generation unit 19C corrects the attenuation of the sound ray signal generated by the beam former 28 of the receiving unit 13 caused by a propagation distance according to the depth of the position where the ultrasonic waves are reflected and performs the envelope detection process on the sound ray signal to generate, as image information data, a signal that is tomographic image information related to the tissues in the subject.

The wireless communication unit 18 of the ultrasound probe 2C modulates a carrier on the basis of the signal generated by the signal processing unit 16 of the image information data generation unit 19C to generate a transmission signal indicating the image information data and wirelessly transmits the generated transmission signal to the wireless communication unit 32 of the diagnostic apparatus main body 3C.

The wireless communication unit 32 of the diagnostic apparatus main body 3C demodulates the transmission signal wirelessly transmitted from the wireless communication unit 18 of the ultrasound probe 2C to acquire the signal generated by the signal processing unit 16 of the image information data generation unit 19C and transmits the signal to the image processing unit 17 of the main-body-side processor 42C.

The image processing unit 17 of the main-body-side processor 42C raster-converts the signal transmitted from the wireless communication unit 32 of the diagnostic apparatus main body 3C into an image signal following the general television signal scanning method and performs various types of necessary image processing, such as brightness correction, gradation correction, sharpness correction, and color correction, on the generated image signal to generate an ultrasound image signal. Further, the image processing unit 17 transmits the generated ultrasound image signal to the display control unit 33 and the measurement unit 36.

The ultrasound image signal transmitted to the display control unit 33 is displayed as the ultrasound diagnostic image on the display unit 34 of the diagnostic apparatus main body 3C under the control of the display control unit 33.

The second image generation unit 37 of the main-body-side processor 42C generates a second image on the basis of the touch position of the user in the image display region RD of the display unit 34 and the ultrasound image U displayed in the image display region RD and displays the generated second image in the image display region RD.

The second image display position determination unit 38 of the main-body-side processor 42C determine a position different from the touch position of the user in the image display region RD as the display position for displaying the second image S on the basis of the touch position of the user in the image display region RD of the display unit 34. Therefore, the second image S does not hinder the touch operation of the user and the user can clearly understand the touch position hidden by the finger F or the like.

As described above, according to the ultrasound system 1C of Embodiment 7, even in a case in which the image processing unit 17 is not provided in the ultrasound probe 2C, but is provided in the diagnostic apparatus main body 3C, as in the aspect of Embodiment 1, the second image generation unit 37 of the main-body-side processor 42C generates the second image S that corresponds to a predetermined region including the touch position of the user in the ultrasound image U displayed in the image display region RD, and the second image display position determination unit 38 determines a position different from the touch position of the user in the image display region RD as the display position for displaying the second image S. In a case in which the image display region RD is touched by the user, the second image S is displayed at the display position in the image display region RD. Therefore, it is possible to effectively display the ultrasound image U while enabling the user to clearly understand the touch position.

In the above-described Embodiments 1 to 6, the ultrasound image signal which has been subjected to the attenuation correction and the envelope detection process by the signal processing unit 16 of the image information data generation unit 19 and then subjected to raster conversion by the image processing unit 17 is wirelessly transmitted as the image information data from the wireless communication unit 18 of the ultrasound probe 2 to the diagnostic apparatus main bodies 3, 3A, and 3B. In Embodiment 7, the signal subjected to the attenuation correction and the envelope detection process by the signal processing unit 16 of the image information data generation unit 19C is wirelessly transmitted as the image information data from the wireless communication unit 18 of the ultrasound probe 2C to the diagnostic apparatus main body 3C. However, it is preferable that the image information data wirelessly transmitted from the ultrasound probe 2 to the diagnostic apparatus main bodies 3, 3A, and 3B and the image information data wirelessly transmitted from the ultrasound probe 2C to the diagnostic apparatus main body 3C are signals after detection. However, the image information data is not limited to the signal after detection.

In addition, in Embodiments 1 to 4, the ultrasound probe 2 and the diagnostic apparatus main body 3 are wirelessly connected to each other. In Embodiment 5, the ultrasound probe 2 and the diagnostic apparatus main body 3A are wirelessly connected to each other. In Embodiment 6, the ultrasound probe 2 and the diagnostic apparatus main body 3B are wirelessly connected to each other. In Embodiment 7, the ultrasound probe 2C and the diagnostic apparatus main body 3C are wirelessly connected to each other. However, the ultrasound probe 2 and the diagnostic apparatus main body 3, 3A, or 3B may be connected to each other in a wired manner, and the ultrasound probe 2C and the diagnostic apparatus main body 3C may be connected to each other in a wired manner. For example, each of the ultrasound probes 2 and 2C and the diagnostic apparatus main bodies 3, 3A, and 3B may be provided with a connection terminal to which a cable capable of transmitting information is connected. The ultrasound probe 2 and the diagnostic apparatus main body 3, 3A, or 3B may be connected to each other by the cable, and the ultrasound probe 2C and the diagnostic apparatus main body 3C may be connected to each other by the cable.

In addition, the aspects of Embodiments 1 to 7 can be applied to portable ultrasound diagnostic apparatuses and can also be applied to stationary ultrasound diagnostic apparatuses.

EXPLANATION OF REFERENCES

1, 1A, 1B, 1C: ultrasound system
2, 2c: ultrasound probe
3, 3A, 3B, 3C: diagnostic apparatus main body
11: transducer array
12: transmitting unit
13: receiving unit
14: transmitting and receiving unit
15: ultrasound transmission and reception control unit
16: signal processing unit
17: image processing unit
18, 32: wireless communication unit
19, 19C: image information data generation unit
20, 35: communication control unit
21, 21C: probe control unit
22: battery
25, 25C: probe-side processor
26: amplification unit
27: AD conversion unit
28: beam former
33: display control unit
34: display unit
36: measurement unit

37: second image generation unit
38: second image display position determination unit
39, 39A, 39B, 39C: main body control unit
40: operation unit
41: storage unit
42, 42A, 42B, 42C: main-body-side processor
43: image size setting unit
44: image cutout unit
45: finger width detection unit
51: second image adjustment unit
52: voice input unit
53: error notification unit
B1: freeze button
B2: storage button
BE: lower edge portion
BL: lower left region
BR: lower right region
C1, C2: measurement cursor
D1: first direction
D2: second direction
F: finger
NL: perpendicular line
R1 to R12: region
RD: image display region
RE: outer region
S: second image
U: ultrasound image
UE: upper edge portion
UL: upper left region
UR: upper right region
W1: horizontal width
W2: vertical width
X1, X2, Y1, Y2: dimension

What is claimed is:

1. An ultrasound system comprising:
a display unit configured to display an acquired ultrasound image as a first image in an image display region;
an operation unit that includes a touch sensor disposed so as to be superimposed on the image display region and is used by a user to perform a touch input operation; and
a first processor configured to:
divide the image display region into a plurality of partial regions,
generate a second image indicating a partial image corresponding to one partial region of the plurality of partial regions including a touch position by the user in the first image displayed in the image display region,
detect a dimension in a predetermined direction of a portion, that is touching on the image display region, of a finger of the user,
set a dimension in the predetermined direction of the second image based on the detected dimension of the finger,
determine a partial region which is not overlapped with the touch position among the plurality of partial regions as a display region which is for displaying the second image, and
display the second image at the display region so as to be superimposed on the first image displayed in the image display region,
wherein the plurality of partial region have a constant dimension in the predetermined direction, and
the first processor is configured to set different dimensions in the predetermined direction of the second image in response to whether the dimension of the finger is larger than the constant dimension.

2. The ultrasound system according to claim 1, wherein the first processor is further configured to: cut out, from the first image, an image which corresponds to the second image.

3. The ultrasound system according to claim 2, wherein the first processor is further configured to: change at least one of the size of the second image or the display region of the second image according to an operation of the user, and display the second image in the image display region.

4. The ultrasound system according to claim 1, wherein the first processor is further configured to: change at least one of the size of the second image or the display region of the second image according to an operation of the user, and display the second image in the image display region.

5. The ultrasound system according to claim 1, wherein the first processor is configured to generate the second image by cutting out, with the set dimension, an image that has the same size as the plurality of partial regions in the first image.

6. The ultrasound system according to claim 1, wherein the first processor is configured to generate the second image by cutting out, with the set dimension, an image obtained by enlarging the one partial region in the first image.

7. The ultrasound system according to claim 1, wherein the first processor is further configured to determine the one partial region which is farthest from a plurality of touch positions among the plurality of partial regions as the display region of the second image.

8. The ultrasound system according to claim 1, further comprising:
an ultrasound probe and a diagnostic apparatus main body that are wirelessly connected to each other, wherein the ultrasound probe includes:
a transducer array;
a second processor configured to:
transmit ultrasonic waves from the transducer array, generate a sound ray signal based on a reception signal acquired by the transducer array, and generate image information data based on the sound ray signal; and
a wireless communication unit configured to wirelessly transmit the image information
data generated by the second processor to the diagnostic apparatus main body, and diagnostic apparatus main body includes:

the display unit configured to display the ultrasound image based on the image information data wirelessly transmitted from the ultrasound probe;
the operation unit; and
the first processor.

9. The ultrasound system according to claim 8, wherein the image information data is a signal obtained by performing attenuation correction according to a depth of a reflection position of the ultrasonic waves and an envelope detection process on the sound ray signal generated by the second processor.

10. The ultrasound system according to claim 8, wherein the image information data is an ultrasound image signal obtained by performing attenuation correction according to a depth of a reflection position of the ultrasonic waves and an envelope detection process on the sound ray signal generated by the second processor and converting the sound ray signal according to a predetermined image display method.

11. A method for controlling an ultrasound system, the method comprising:
displaying an acquired ultrasound image as a first image in an image display region;
dividing the image display region into a plurality of partial regions;
generating a second image indicating a partial image corresponding to one partial region of the plurality of partial regions including a touch position by the user in the first image displayed in the image display region;
detecting a dimension in a predetermined direction of a portion, that is touching on the image display region, of a finger of the user;
setting a dimension in the predetermined direction of the second image based on the detected dimension of the finger;
determining a partial region which is not overlapped with the touch position among the plurality of partial regions as a display region which is for displaying the second image; and
displaying the second image at the display region so as to be superimposed on the first image displayed in the image display region,
wherein the plurality of partial region have a constant dimension in the predetermined direction, and
the method comprises setting different dimensions in the predetermined direction of the second image in response to whether the dimension of the finger is larger than the constant dimension.

* * * * *